US012383393B2

(12) United States Patent
Peyman

(10) Patent No.: US 12,383,393 B2
(45) Date of Patent: Aug. 12, 2025

(54) ABLATABLE CORNEAL INLAY FOR CORRECTION OF REFRACTIVE ERRORS AND/OR PRESBYOPIA

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 759 days.

(21) Appl. No.: 17/683,344

(22) Filed: Feb. 28, 2022

(65) Prior Publication Data

US 2022/0409361 A1   Dec. 29, 2022

Related U.S. Application Data

(63) Continuation-in-part of application No. 16/927,882, filed on Jul. 13, 2020, now Pat. No. 11,259,914, which is a continuation-in-part of application No. 15/422,914, filed on Feb. 2, 2017, now Pat. No. 10,709,546, which is a continuation-in-part of application No. 15/230,445, filed on Aug. 7, 2016, now Pat. No. 9,937,033, which is a
(Continued)

(51) Int. Cl.
*A61F 2/14* (2006.01)
*A61F 2/00* (2006.01)
*A61F 9/00* (2006.01)
*A61F 9/008* (2006.01)

(52) U.S. Cl.
CPC ............ *A61F 2/1451* (2015.04); *A61F 2/148* (2013.01); *A61F 9/0017* (2013.01); *A61F 9/008* (2013.01); *A61F 9/00802* (2013.01); *A61F 9/00804* (2013.01); *A61F 9/00808* (2013.01); *A61F 9/00812* (2013.01); *A61F 2002/0081* (2013.01); *A61F 2240/002* (2013.01)

(58) Field of Classification Search
CPC .... A61F 9/0079; A61F 9/008; A61F 9/00804; A61F 9/00808; A61F 9/00812; A61F 9/00821; A61F 9/00827; A61F 9/00834; A61F 2009/00872; A61F 2009/00893; A61F 2/145; A61F 2/1451; A61F 2/1453
See application file for complete search history.

(56) References Cited

U.S. PATENT DOCUMENTS 3,760,807 A   9/1973   Neefe
4,563,779 A   1/1986   Kelman
(Continued)

FOREIGN PATENT DOCUMENTS

WO   89/04153 A1   5/1989
WO   92/16172 A1   10/1992
(Continued)

OTHER PUBLICATIONS

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).
(Continued)

*Primary Examiner* — William H Matthews
(74) *Attorney, Agent, or Firm* — The Law Office of Patrick F. O'Reilly III, LLC

(57) ABSTRACT

An ablatable corneal inlay for correction of refractive errors and/or presbyopia, and a method of correcting refractive errors and presbyopia in an eye of a patient using an ablatable corneal inlay is disclosed herein.

15 Claims, 23 Drawing Sheets

Related U.S. Application Data continuation-in-part of application No. 14/709,801, filed on May 12, 2015, now Pat. No. 9,427,355.

(60) Provisional application No. 63/026,033, filed on May 16, 2020, provisional application No. 62/360,281, filed on Jul. 8, 2016, provisional application No. 62/290,089, filed on Feb. 2, 2016, provisional application No. 62/065,714, filed on Oct. 19, 2014, provisional application No. 61/991,785, filed on May 12, 2014.

(56) References Cited

U.S. PATENT DOCUMENTS

| | | | |
|---|---|---|---|
| 4,665,913 | A | 5/1987 | L'Esperance, Jr. |
| 4,718,418 | A | 1/1988 | L'Esperance, Jr. |
| 4,793,344 | A | 12/1988 | Cumming et al. |
| 4,799,931 | A | 1/1989 | Lindstrom |
| 4,840,175 | A | 6/1989 | Peyman |
| 4,903,695 | A | 2/1990 | Warner et al. |
| 4,994,058 | A | 2/1991 | Raven et al. |
| 4,994,080 | A | 2/1991 | Shepard |
| 5,171,318 | A | 12/1992 | Gibson et al. |
| 5,245,367 | A | 9/1993 | Miller et al. |
| 5,336,261 | A | 8/1994 | Barrett et al. |
| 5,552,452 | A | 9/1996 | Khadem |
| 5,702,441 | A | 12/1997 | Zhou |
| 5,905,561 | A | 5/1999 | Lee et al. |
| 5,964,748 | A | 10/1999 | Peyman |
| 6,110,166 | A | 8/2000 | Juhasz |
| 6,180,687 | B1 | 1/2001 | Hammer |
| 6,197,019 | B1 | 3/2001 | Peyman |
| 6,537,545 | B1 | 3/2003 | Karageozian et al. |
| 6,551,307 | B2 | 4/2003 | Peyman |
| 7,001,374 | B2 | 2/2006 | Peyman |
| 7,004,902 | B2 | 2/2006 | Luce |
| 7,044,945 | B2 | 5/2006 | Sand |
| 9,301,925 | B2 | 4/2016 | Xu et al. |
| 9,370,446 | B2 | 6/2016 | Peyman |
| 9,814,567 | B2 | 11/2017 | Peyman |
| 10,660,743 | B2 | 5/2020 | Peyman et al. |
| 10,925,723 | B2 | 2/2021 | Peyman et al. |
| 11,596,513 | B2 | 3/2023 | Peyman et al. |
| 2001/0027314 | A1 | 10/2001 | Peyman |
| 2002/0006394 | A1 | 1/2002 | Redmond et al. |
| 2002/0071856 | A1 | 6/2002 | Dillingham |
| 2003/0035843 | A1 | 2/2003 | Livesey et al. |
| 2004/0029855 | A1 | 2/2004 | Klaveness et al. |
| 2005/0246018 | A1 | 11/2005 | Grubbs |
| 2006/0135477 | A1 | 6/2006 | Haitjema |
| 2007/0135754 | A1 | 6/2007 | Akiyama et al. |
| 2007/0142908 | A1 | 6/2007 | Xu |
| 2007/0255404 | A1 | 11/2007 | Pinchuk |
| 2009/0030513 | A1 | 1/2009 | Valyunin |
| 2009/0171305 | A1 | 7/2009 | El Hage |
| 2009/0208577 | A1 | 8/2009 | Xu et al. |
| 2010/0198348 | A1 | 8/2010 | Hiles et al. |
| 2010/0210996 | A1 | 8/2010 | Peyman |
| 2010/0215717 | A1 | 8/2010 | Soker et al. |
| 2011/0040376 | A1 | 2/2011 | Christie et al. |
| 2011/0076734 | A1 | 3/2011 | Zhou et al. |
| 2011/0152219 | A1 | 6/2011 | Stagni et al. |
| 2011/0166650 | A1 | 7/2011 | Busin |
| 2011/0208300 | A1 | 8/2011 | de Juan, Jr. et al. |
| 2011/0250688 | A1 | 10/2011 | Hasan |
| 2011/0295367 | A1 | 12/2011 | Cuevas |
| 2012/0203161 | A1 | 8/2012 | Herekar |
| 2012/0226351 | A1 | 9/2012 | Peyman |
| 2013/0053955 | A1 | 2/2013 | Currie |
| 2014/0142200 | A1 | 5/2014 | Duan et al. |
| 2014/0277437 | A1 | 9/2014 | Currie |
| 2014/0379078 | A1 | 12/2014 | Trindade |
| 2016/0022495 | A1 | 1/2016 | Feingold |
| 2016/0067035 | A1 | 3/2016 | Gontijo |
| 2016/0331868 | A1 | 11/2016 | Grubbs et al. |
| 2017/0007395 | A1 | 1/2017 | Peyman |
| 2017/0273779 | A1 | 9/2017 | Zhao |

FOREIGN PATENT DOCUMENTS

| | | |
|---|---|---|
| WO | 01/58495 A2 | 8/2001 |
| WO | 2008/055118 A2 | 5/2008 |

OTHER PUBLICATIONS

Wollensak et al., "Riboflavin/Ultraviolet-A—induced Collagen Crosslinking for the Treatment of Keratoconus", American Journal of Ophthalmology, vol. 135, pp. 620-627 (2003).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010;17(4): pp. 349-353.

Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).

First office action on the merits (Non-Final Rejection) in U.S. Appl. No. 14/709,801, mailed on Jan. 11, 2016.

Second office action on the merits (Final Rejection) in U.S. Appl. No. 14/709,801, mailed on May 4, 2016.

Notice of Allowance in U.S. Appl. No. 14/709,801, mailed on Jul. 19, 2016.

First office action on the merits (Non-Final Rejection) in U.S. Appl. No. 15/230,445, mailed on Jul. 11, 2017.

Notice of Allowance in U.S. Appl. No. 15/230,445, mailed on Dec. 4, 2017.

First office action on the merits (Non-Final Rejection) in U.S. Appl. No. 15/422,914, mailed on Oct. 18, 2019.

Notice of Allowance in U.S. Appl. No. 15/422,914, mailed on Mar. 17, 2020.

First office action on the merits (Non-Final Rejection) in U.S. Appl. No. 16/927,882, mailed on Sep. 28, 2021.

Notice of Allowance in U.S. Appl. No. 16/927,882 mailed on Oct. 25, 2021.

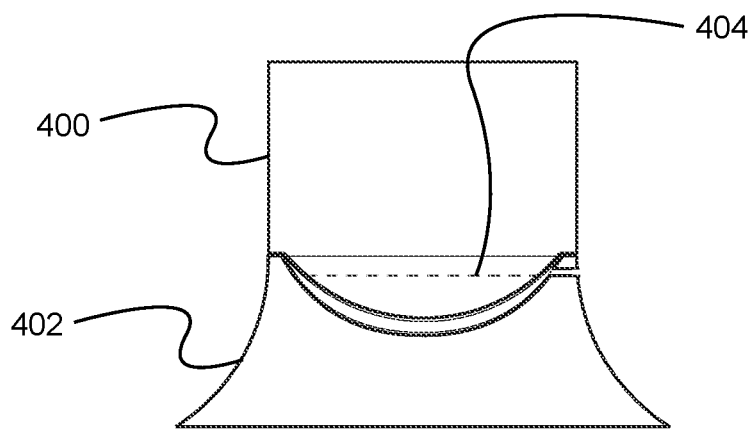
FIG. 28
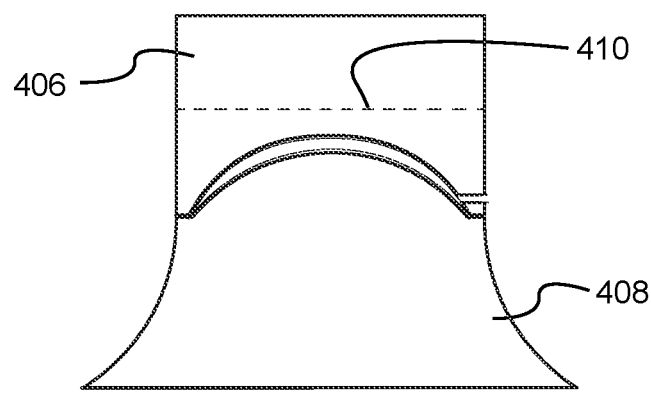
FIG. 29
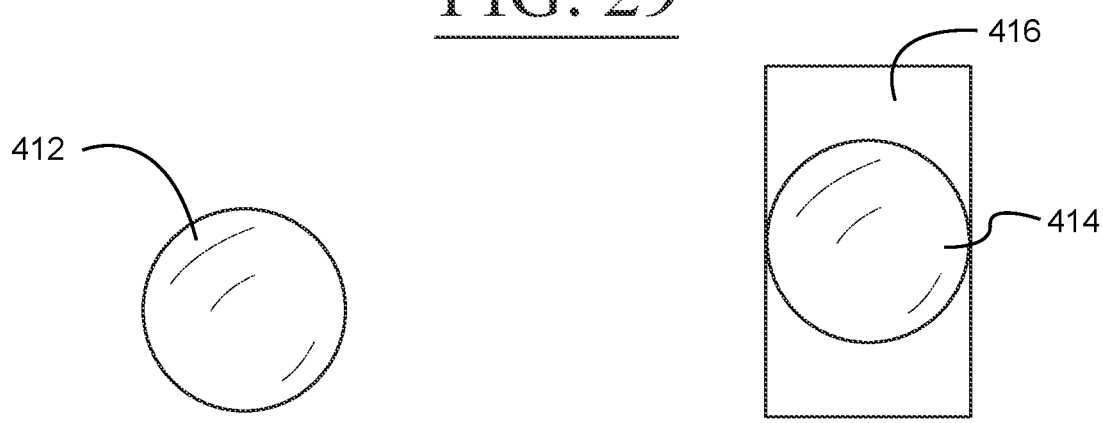
FIG. 30
FIG. 31

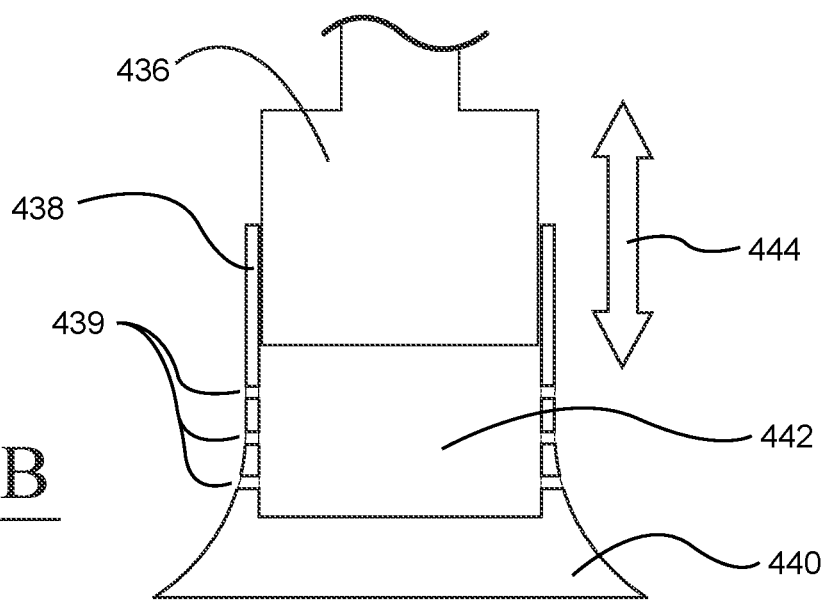
FIG. 33B
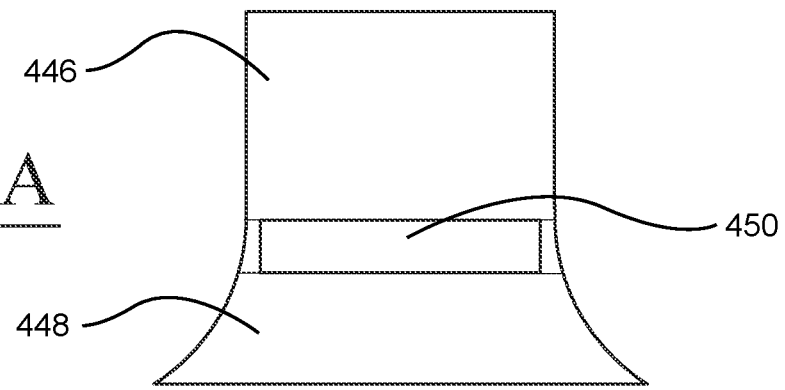
FIG. 34A
FIG. 34B
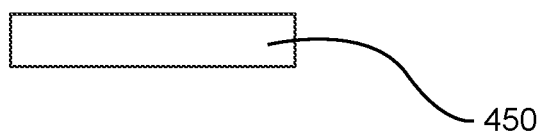

ABLATABLE CORNEAL INLAY FOR CORRECTION OF REFRACTIVE ERRORS AND/OR PRESBYOPIA

CROSS-REFERENCE TO RELATED APPLICATIONS

This patent application is a continuation-in-part of application Ser. No. 16/927,882, entitled "Molding or 3-D Printing of a Synthetic Refractive Corneal Lenslet", filed Jul. 13, 2020, which claims priority to U.S. Provisional Patent Application No. 63/026,033, entitled "Molding or 3-D Printing of a Synthetic Refractive Corneal Lenslet", filed on May 16, 2020, and is a continuation-in-part of application Ser. No. 15/422,914, entitled "Intracorneal Lens Implantation With A Cross-Linked Cornea", filed on Feb. 2, 2017, now U.S. Pat. No. 10,709,546, which claims priority to U.S. Provisional Patent Application No. 62/290,089, entitled "Method of Altering the Refractive Properties of the Eye", filed on Feb. 2, 2016, and is a continuation-in-part of application Ser. No. 15/230,445, entitled "Corneal Lenslet Implantation With A Cross-Linked Cornea", filed Aug. 7, 2016, now U.S. Pat. No. 9,937,033, which claims priority to U.S. Provisional Patent Application No. 62/360,281, entitled "Method of Altering the Refractive Properties of an Eye", filed on Jul. 8, 2016, and is a continuation-in-part of application Ser. No. 14/709,801, entitled "Corneal Transplantation With A Cross-Linked Cornea", filed May 12, 2015, now U.S. Pat. No. 9,427,355, which claims priority to U.S. Provisional Patent Application No. 61/991,785, entitled "Corneal Transplantation With A Cross-Linked Cornea", filed on May 12, 2014, and to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to forming a synthetic refractive corneal lenslet. More particularly, the invention relates to molding or 3-D printing of a synthetic refractive corneal lenslet.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, and other corneal dystrophies. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea converting an image of the point of light to a line. Therefore, an astigmatic eye is incapable of sharply focusing images on the retina.

While laser surgical techniques, such as laser-assisted in situ keratomileusis (LASIK) and photorefractive keratectomy (PRK) are known for correcting refractive errors of the eye, these laser surgical techniques have complications, such as post-operative pain and dry eye. Also, these laser surgical techniques cannot be safely used on patients with corneas having certain biomechanical properties. For example, corneal ectasia may occur if these laser surgical techniques are applied to patients having thin corneas (e.g., corneas with thicknesses that are less than 500 microns).

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells. Also, what is needed is a method for corneal lenslet implantation for modifying the cornea to better correct ametropic conditions. In addition, a method is needed for corneal lenslet implantation that prevents a lens implant from moving around inside the cornea once implanted so that the lens implant remains centered about the visual axis of the eye. Further, what is needed is a method for intracorneal lens implantation for modifying the cornea to better correct ametropic conditions.

In addition, numerous corneal diseases affect the clarity of the cornea necessitating partial or full thickness corneal replacement. These diseases are generally inherited affecting the cornea but no other organs. The disorders can involve one part of the cornea, but subsequently spread to the neighboring layers. Among the genetic disease involving corneal endothelial cells are Fuchs endothelial dystrophy, hereditary endothelial posterior polymorphic dystrophy, etc. causing damage to the corneal endothelial cells which prevent flooding of the cornea with aqueous fluid and producing the cloudiness of the normally transparent corneal stroma. Other genetic diseases involve the corneal stroma, such as granular corneal dystrophy, macular corneal dystrophy, Schneider crystalline dystrophy, and lattice corneal dystrophy, etc. all blocking or distorting the light that passes through the cornea on way to reach the sensory retina. Others conditions, such as keratoconus and keratoglobus, affect the mechanical stability of the cornea to resist the intraocular pressure. With time the cornea expands and can rupture without a surgical intervention of a corneal transplantation. The other genetic diseases affect the anterior layer of the cornea, the bowman layer of the cornea or the corneal epithelium, such as in Meesmann juvenile epithelial dystrophy, epithelial basement membrane dystrophy, gelatinous drop-like dystrophy, Lisch epithelial corneal dystrophy and Reis-Bucklers corneal dystrophy, and genetic recurrent corneal erosion. However, a number of other conditions can cause damage to the cornea, which results in losing its transparency, e.g., after, injuries, infections, corneal ulcers, or previous cataract surgeries or glaucoma surgeries.

At present about less than 200,000 corneal transplantations are performed each year in the world, but more than 12 million people are in need of corneal transplantation. This discrepancy is created by the need for surgery and unavailability of corneas for transplantation. Some of the reasons stem from the religious beliefs refusing another person's tissue, but most importantly, the retrieved human corneas from human eye banks can be stored only for a limited time which is at present is about 11 days. Even if only a part of the cornea is used for lamellar keratoplasty which requires the corneal stroma, the remaining part of the cornea must be discarded. The use of an animal cornea is not tolerated in humans. In addition, roughly about 10% of human corneal transplants can be rejected by the patients because of the incompatibility of the tissue.

Therefore, there is a further need to reduce the burden of corneal availability by producing synthetic corneal stromal lenslets that at least can be used for partial lamellar transplantation, in patients who have a limited corneal scared stroma after injury and infection. In addition, there is a need to address the growing need in refractive surgery to modify the refractive power of the cornea by a biocompatible refractive partial cornea or lenslet. Obtaining these corneas from the eye bank has been described in previous patents by the present inventor (see e.g., U.S. Pat. Nos. 10,314,690 and 10,583,221, which are hereby incorporated by reference as if set forth in their entirety herein). However, the need for refractive surgery is more than for corneal transplantation. Using the eye bank corneas for creating a lenslet would eliminate their badly needed indications described for patients that require them.

At present, over five million refractive surgeries are done in the world for myopia, hyperopia, astigmatism, keratoconus or keratoglobus eyes. Practically all presently available refractive procedures require ablating a part of the cornea or removing a part of the corneal stroma which thins out these corneas and can potentially lead to ectasia of the corneas, e.g., after the LASIK procedure, etc. leading to the need for a corneal transplantation.

Further, patients above the age of 45 years generally are not considered a candidate for corneal refractive surgery, such as LASIK or SMILE procedures. These two procedures remove a part of the corneal stroma with an excimer laser or femtosecond laser to correct the refractive errors of the eye defocus and astigmatism for the patient to see the far object without the use of glasses.

In young people below the age of 45, the crystalline lens of the eye has the ability to change its shape by ciliary muscles that contracts and relaxes the myriads of microns thick cords called zonules that are attached to the crystalline lens capsule and from another end to the ciliary muscle and suspend the crystalline lens behind the iris, in the posterior chamber of the eye. The circular contraction of the ciliary muscle loosens the zonules and as a result the crystalline lens becomes more convex. This process is called accommodation, by which the near object in front of the eye, such as a newspaper, becomes in focus for the retina to see the letters sharp for reading. This process enables the person to see any object from infinity to about 30 cm sharp as long as the crystalline lens is flexible. However with aging, the crystalline lens becomes more rigid and the eye cannot accommodate to see the near objects sharp.

Since the standard LASIK and SMILE procedures do not correct presbyopia, the ophthalmologist normally recommends the patient wait until the lens becomes a cataract that can be removed and replaced with a multifocal intraocular lens (IOL), which to some degree, provides sharp images at focal points from the eye at various distances.

Though LASIK surgery for presbyopia can convert the refractive power of one eye to see near objects and the other eye to see far objects, the so-called monovision, it is not tolerated by most people and reduces, to some degree, the stereovision. The scleral-based surgery is another attempt to correct presbyopia but it is the least predictable.

Therefore, there is a further need for an ablatable corneal inlay that is capable of simultaneous correction of refractive errors and presbyopia.

BRIEF SUMMARY OF EMBODIMENTS OF THE INVENTION

Accordingly, the present invention is directed to an ablatable corneal inlay for correction of refractive errors and/or presbyopia and a method of using the ablatable corneal inlay that substantially obviates one or more problems resulting from the limitations and deficiencies of the related art.

In accordance with one or more embodiments of the present invention, there is provided a method of correcting refractive errors and presbyopia in an eye of a patient using an ablatable corneal inlay. The method includes the steps of: (i) forming a darkened annular area in a central region of a corneal inlay so as to define a central pinhole for correcting presbyopia in a host eye of a patient, the darkened annular area being generally non-transparent; (ii) forming a flap or a pocket for receiving the corneal inlay in the cornea of the host eye of the patient; (iii) inserting the corneal inlay into the pocket or on stromal tissue exposed by the flap in the cornea of the host eye of the patient; (iv) modifying the shape of the corneal inlay using a laser so that the corneal inlay is capable of correcting refractive errors in the host eye of the patient; (v) applying a photosensitizer to the cornea of the host eye of the patient so that the photosensitizer permeates at least a portion of the host corneal tissue surrounding the corneal inlay and/or at least a portion of the corneal inlay; and (vi) irradiating the cornea so as to activate cross-linkers in the corneal inlay and/or cross-linkers in the portion of the host corneal tissue surrounding the corneal inlay, and thereby prevent an immune response from the patient, prevent rejection of the corneal inlay by the patient, and/or strengthen the biomechanical properties of the corneal inlay. The corneal inlay is configured to simultaneously correct refractive errors and presbyopia in the host eye of the patient.

In a further embodiment of the present invention, the step of forming the darkened annular area in the central region of the corneal inlay comprises forming the darkened annular area in the central region of the corneal inlay by tattooing using a biocompatible, non-toxic dark or black ink.

In yet a further embodiment, the step of forming the darkened annular area in the central region of the corneal inlay comprises forming the darkened annular area in the central region of the corneal inlay by means of a darkened polymeric ring that is 3D printed with the corneal inlay.

In still a further embodiment, the step of forming the darkened annular area in the central region of the corneal inlay comprises forming the darkened annular area in the central region of the corneal inlay by inserting a sharp-edged cylinder with darkened outer walls into the corneal inlay.

In yet a further embodiment, the step of forming the darkened annular area in the central region of the corneal inlay comprises forming the darkened annular area in the central region of the corneal inlay by creating a central aperture in the corneal inlay, and then subsequently tattooing a bounding wall of the central aperture using a biocompatible, non-toxic dark or black ink.

In still a further embodiment, the step of forming the darkened annular area in the central region of the corneal inlay comprises forming the darkened annular area in the central region of the corneal inlay by creating a virtual pinhole in the corneal inlay by tattooing using a biocompatible, non-toxic dark or black ink or by 3D printing the virtual pinhole.

In yet a further embodiment, the corneal inlay is formed from a collagen solution using a mold or a 3-D printer, the mold or the 3-D printer being configured to form the corneal inlay into a predetermined shape for correcting a particular refractive error of the patient.

In still a further embodiment, the corneal inlay is formed using the 3-D printer, the 3-D printer including a nozzle for forming the corneal inlay in layers from a collagen solution, and the 3-D printer being under the control of a data processing device so as to form the corneal inlay into a predetermined shape for correcting a particular refractive error of the patient.

In yet a further embodiment, the step of applying the photosensitizer into the cavity of the eye of the patient further comprises applying riboflavin to the cornea of the eye of the patient so that the riboflavin permeates at least a portion of the host corneal tissue surrounding the corneal inlay and/or at least a portion of the corneal inlay; and the step of irradiating the cornea so as to activate cross-linkers in the corneal inlay and/or cross-linkers in the portion of the tissue surrounding the cavity further comprises irradiating the cornea with ultraviolet radiation so as to activate cross-linkers in the corneal inlay and/or cross-linkers in the portion of the host corneal tissue surrounding the corneal inlay.

In still a further embodiment, the step of modifying the shape of the corneal inlay using the laser comprises ablating the corneal inlay using an excimer laser or a femtosecond laser under the control of a Shack-Hartmann wavefront system and a data processing device so as to modify the corneal inlay to the desired refractive power so that the corneal inlay corrects refractive error of the eye as desired for hyperopia, myopia, astigmatism, or presbyopia after its implantation.

In yet a further embodiment, the corneal inlay is formed from an animal cornea.

In still a further embodiment, the corneal inlay is decellularized using chemical means, the chemical means for destroying the cellular elements in the corneal inlay are selected from the group consisting of ethanol, glycerol, acids, alkalis, peracetic acid, ammonium hydroxide ionic detergents, sodium dodecyl sulfate, sodium deoxycholate non-ionic detergents, zwitterionic detergents, Triton X-100, benzalkonium chloride, Igepal, genipin, and combinations thereof.

In yet a further embodiment, the corneal inlay is formed from a human cornea.

In still a further embodiment, the step of forming a flap or a pocket for receiving the corneal inlay in the cornea of the host eye of the patient comprises forming the flap in the cornea of the host eye of the patient for receiving the corneal inlay.

In yet a further embodiment, the step of forming a flap or a pocket for receiving the corneal inlay in the cornea of the host eye of the patient comprises forming the pocket in the cornea of the host eye of the patient for receiving the corneal inlay.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 28 is a side view of a mold being used to form a synthetic concave lenslet;

FIG. 29 is a side view of a mold being used to form a synthetic convex lenslet;

FIG. 30 is a top view of a circular lenslet;

FIG. 31 is a top view of a circular lenslet optic with a rectangular peripheral edge;

FIG. 33B is a side view of a mold with a plunger for compressing the collagen hydrogel disposed in the mold;

FIG. 34A is a side view of a mold being used to form a synthetic lenslet with parallel front and back surfaces;

FIG. 34B is a side view of the synthetic lenslet with parallel front and back surfaces formed by the mold;

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
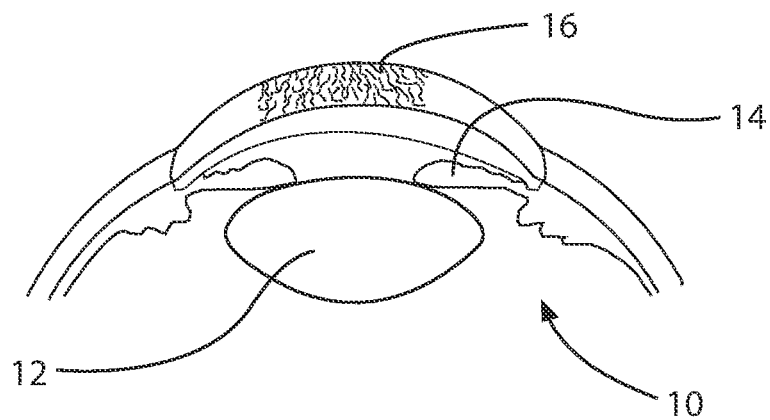
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
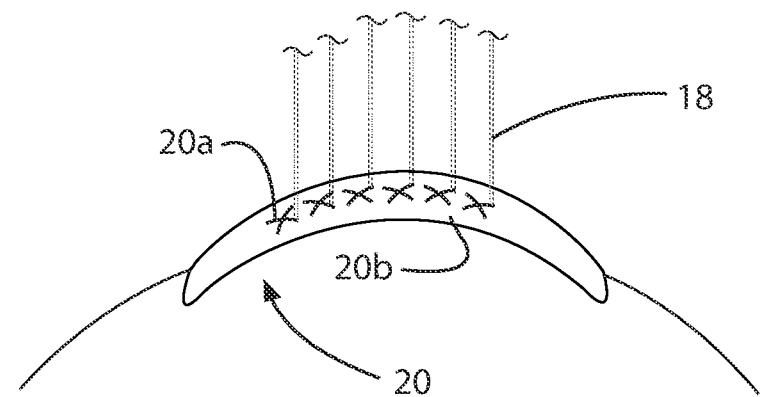
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front portion 20a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the cross-linking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The crosslinker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
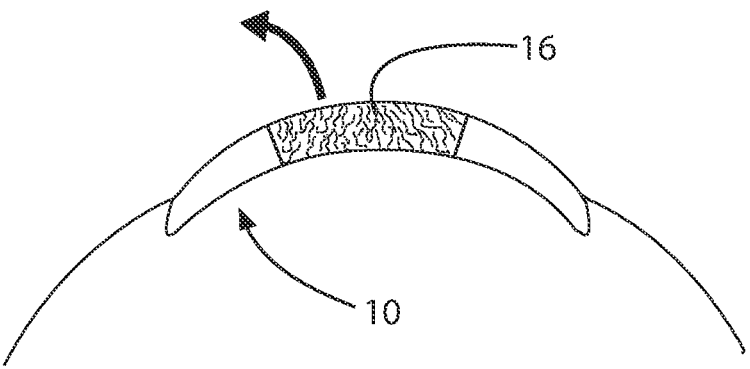
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
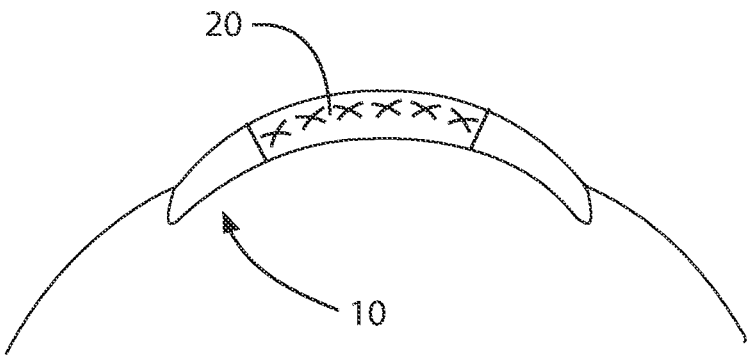
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a non-cross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

Figure 2A:
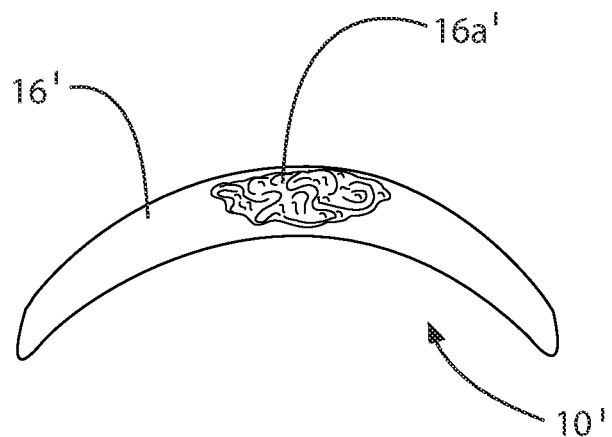
FIG. 2A is a partial side cross-sectional view of an eye having internal corneal scar tissue.
Figure 2B:
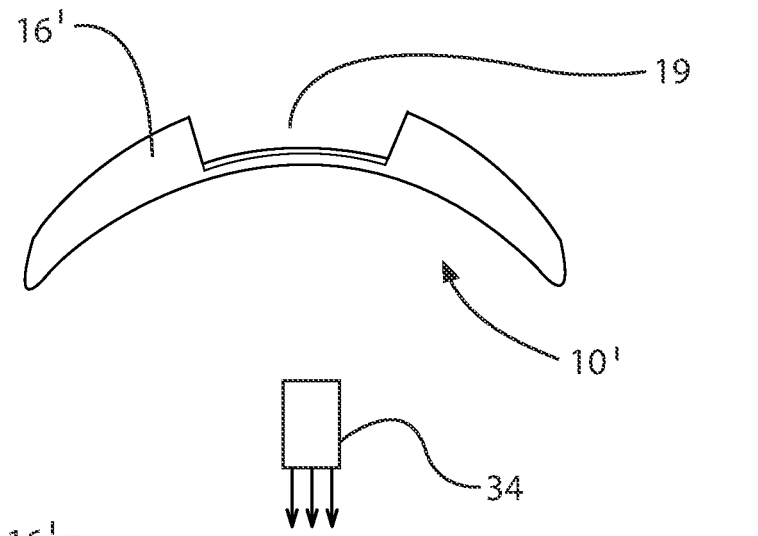
FIG. 2B is a partial side cross-sectional view of the eye of FIG. 2A, wherein the scarred corneal tissue has been externally removed from the eye.
Figure 2C:
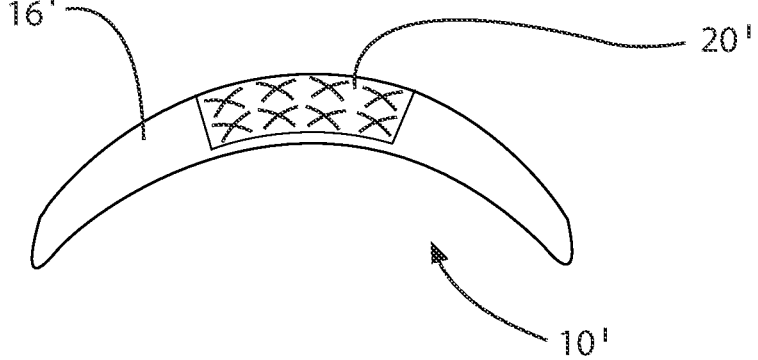
FIG. 2C is a partial side cross-sectional view of the eye of FIG. 2A, wherein a cross-linked donor cornea is shown being implanted in the location previously occupied by the scarred corneal tissue.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
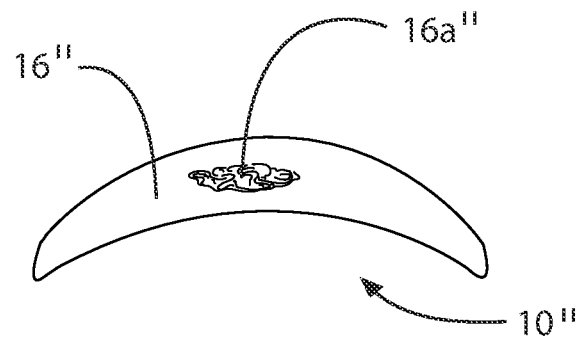
FIG. 3A is a partial side cross-sectional view of an eye having internal corneal scar tissue.
Figure 3B:
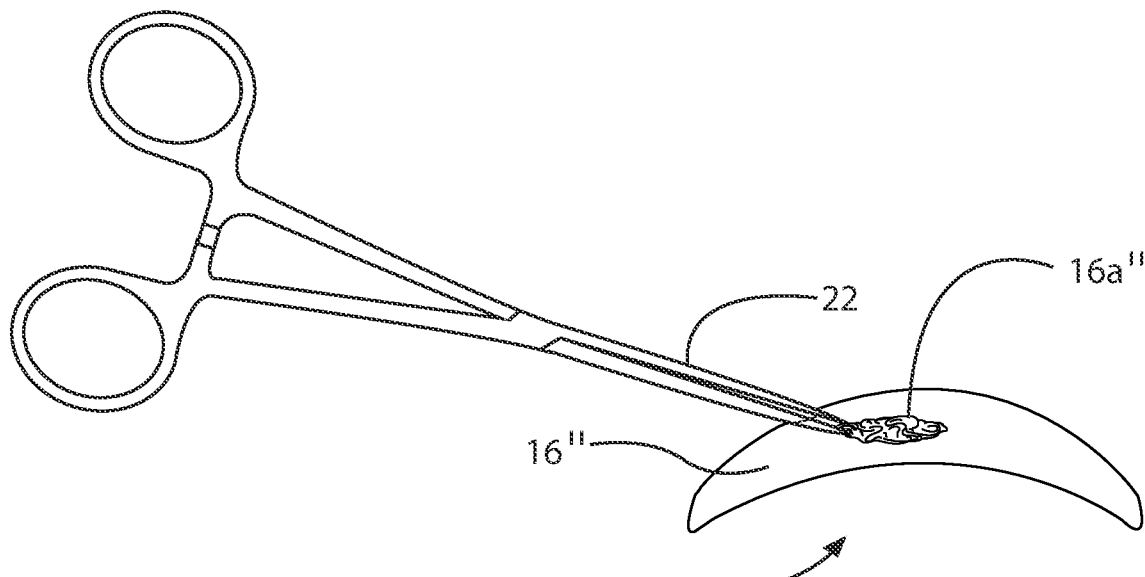
FIG. 3B is a partial side cross-sectional view of the eye of FIG. 3A, wherein the scarred corneal tissue is shown being internally removed from the eye.
Figure 3C:
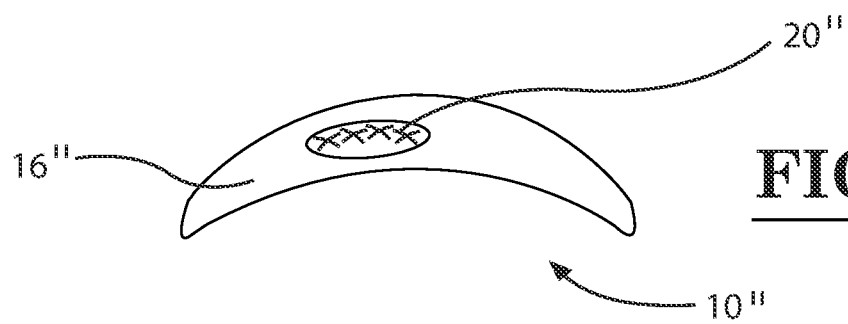
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a''' of the cornea 16''' with a donor corneal portion. Thus, similar to the second and third embodiments explained above, FIGS. 4A-4E illustrate a lamellar keratoplasty procedure wherein only a portion of the cornea 16''' of the eye 10''' contains scarred and/or diseased tissue (i.e., a full-thickness corneal section is not removed). Although, in the procedure of FIGS. 4A-4E, a different-shaped scarred and/or diseased portion 16a''' of the cornea 16''' is removed.

Figure 4A:
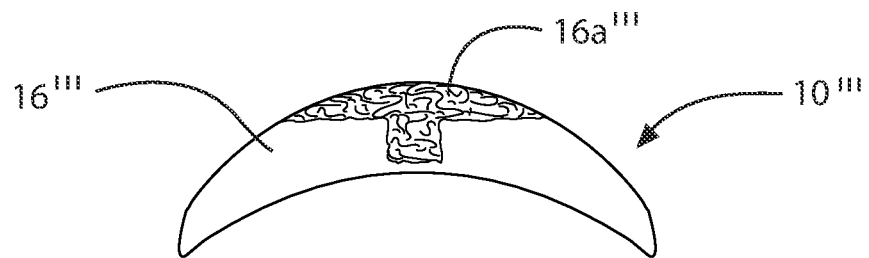
FIG. 4A is a partial side cross-sectional view of an eye having a T-shaped corneal scar and/or diseased tissue portion.

Referring initially to FIG. 4A, it can be seen that only a portion 16a''' of the cornea 16''' having a T-shape or "top hut" shape is scarred and/or diseased. As such, in this embodiment, it is not necessary to replace the entire thickness of the cornea 16''' with a donor cornea as was described above in conjunction with FIGS. 1A-1D, but rather just a portion 16a''' of the cornea 16'''. In this illustrative embodiment, the back side of the cornea 16''' is maintained (see e.g., FIG. 4D).

Figure 4B:
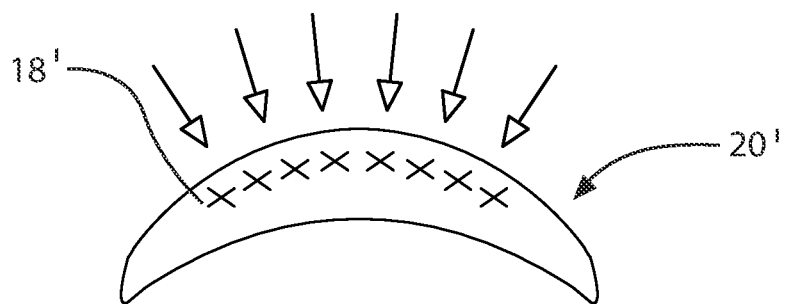
FIG. 4B is another partial side cross-sectional view of a donor cornea undergoing cross-linking.
Figure 4C:
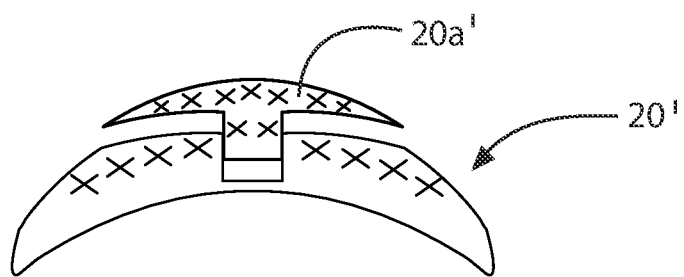
FIG. 4C is a partial side cross-sectional view illustrating a T-shaped portion of the cross-linked donor cornea being cut out from a remainder of the donor cornea.
Figure 5A:
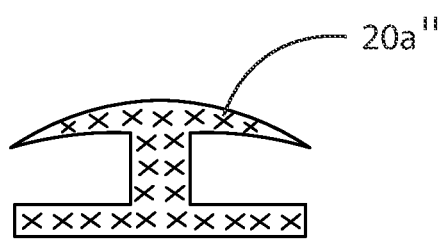
FIG. 5A illustrates an alternative configuration for the cross-linked donor cornea implant, wherein the donor cornea implant has a dumbbell shape.
Figure 5B:
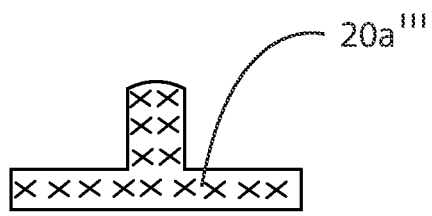
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a''' of the cornea 16''', is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a'' (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
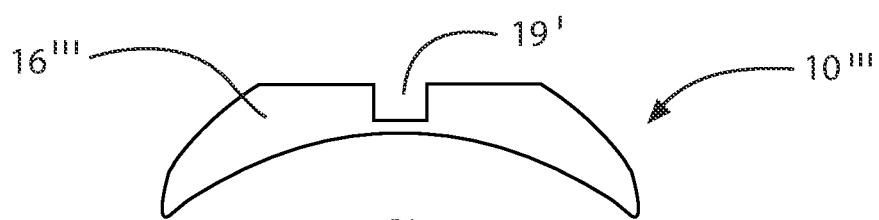
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16a''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16a''' may be removed from the remainder of the cornea 16''' using various suitable means, such as mechanical means or the laser cutting means (e.g., femtosecond laser) described above.

Figure 4E:
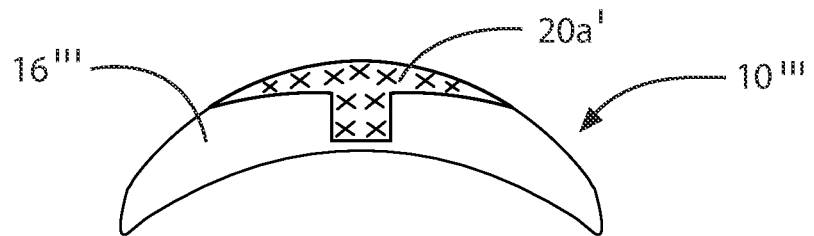
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16a''' has been removed from the remainder of the cornea 16''' of the eye 10''', the cross-linked donor corneal portion 20a' is implanted into the eye 10''' of the patient in the location previously occupied by the scarred and/or diseased corneal portion 16a'''. Because the shape of the transplant corresponds to that of the removed portion 16a''' of the cornea 16''', the transplant sits comfortably in its position in the host cornea. As described above, after implantation of the cross-linked donor corneal portion 20a' into the eye 10''', sutures or a suitable adhesive (e.g., the biocompatible and biodegradable adhesive described above) may be utilized to secure the cross-linked donor corneal portion 20a' in place on the host cornea 16''' of the eye 10'''. For example, if a biocompatible and biodegradable adhesive is used to secure the cross-linked donor corneal portion 20a' in place in the cornea 16''' of the eye 10''', the edges of the donor corneal portion 20a' are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

An illustrative embodiment of a corneal lenslet implantation procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16"" of the host eye 10"" is removed during the procedure (i.e., a full-thickness corneal section is not removed). Although, the procedure of FIGS. 6A-6C and 7A-7C differs in several important respects from the above described procedures. In this embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16"" of the host eye 10"". After making an internal pocket 28 in the recipient cornea 16"" of the host eye 10"" with a femtosecond laser, the cross-linked transplant is folded and implanted in a predetermined fashion inside the host's corneal pocket 28 to provide stability to the eye 10"" having keratoconus, keratoglobus, a thin cornea or abnormal corneal curvature, thereby preventing future corneal ectasia in this eye 10"" and correcting its refractive errors. Advantageously, the procedure of this embodiment comprises a lamellar cross-linked corneal transplantation, which additionally results in simultaneous correction of the refractive error of the eye 10"" of the patient. As used herein, the term "lenslet" refers to a lens implant configured to be implanted in a cornea of an eye. The lens implant may be formed from an organic material, a synthetic material, or a combination of organic and synthetic materials.

Figure 6A:
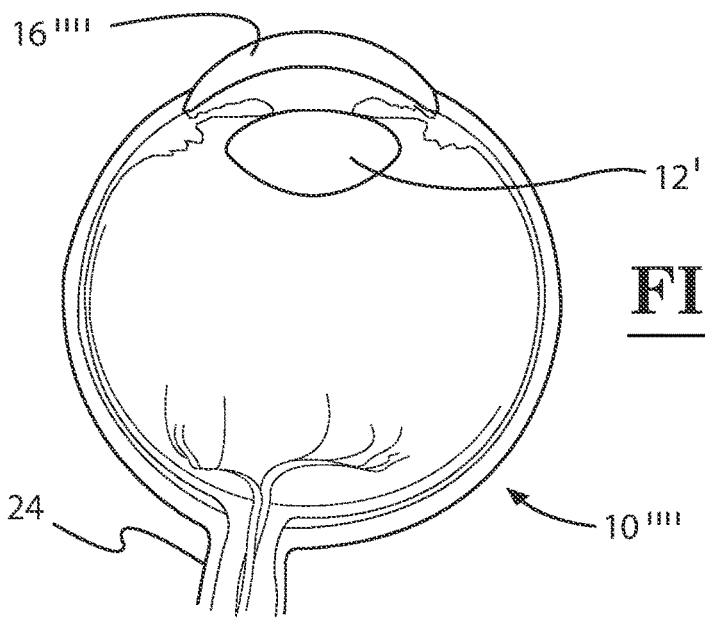
FIG. 6A is a side cross-sectional view of a host eye prior to an transplant procedure.
Figure 6B:
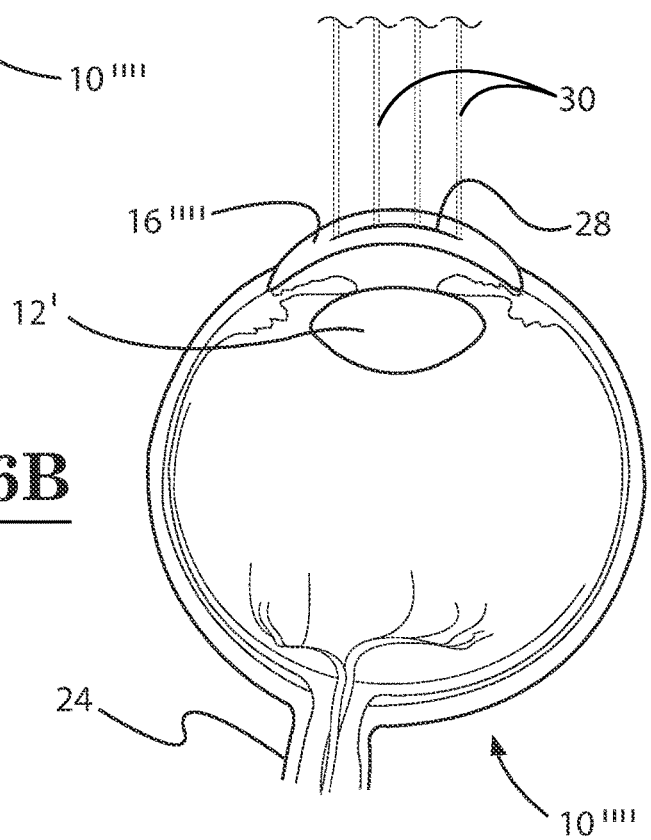
FIG. 6B is another side cross-sectional view of the host eye of FIG. 6A, which illustrates a creation of a corneal pocket therein.

Now, with reference to FIGS. 6A-6C and 7A-7C, the illustrative embodiment will be described in further detail. The host eye 10"" with lens 12', cornea 16"", and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16"" of the host eye 10"" (e.g., by using a suitable laser, which is indicated diagrammatically in FIG. 6B by lines 30).

Figure 7A:
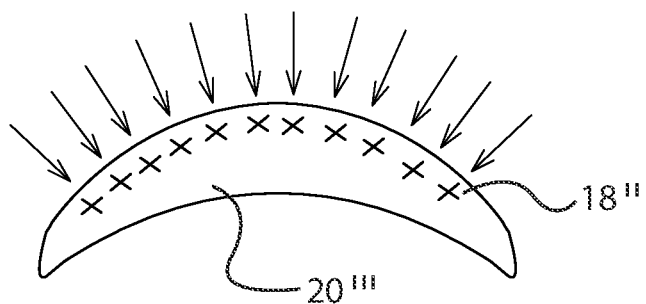
FIG. 7A is a partial side cross-sectional view of a donor cornea being cross-linked prior to being shaped for use in a transplant procedure.
Figure 7B:
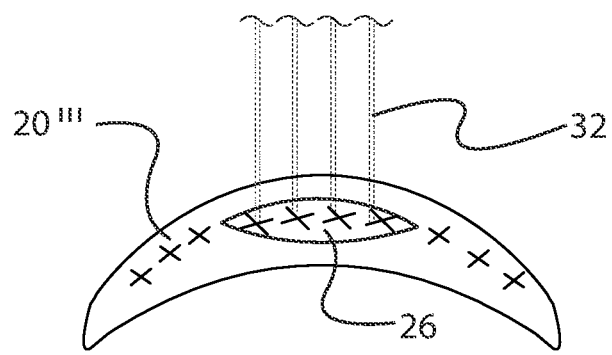
FIG. 7B is another partial side cross-sectional view of the donor cornea of FIG. 7A, which illustrates the cutting of a cross-linked lamellar lenslet from a remainder of the cross-lined donor cornea.
Figure 7C:
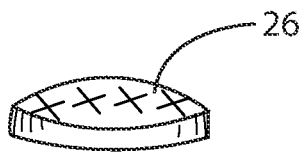
FIG. 7C is a side cross-sectional view of the cross-linked lamellar lenslet after it has been appropriately shaped and removed from the donor cornea of FIGS. 7A and 7B.

In FIG. 7A, the cross-linking 18" of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked (e.g., by using a photosensitizer in the form of riboflavin and UV radiation as described above), it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10"". As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20'''.

Figure 6C:
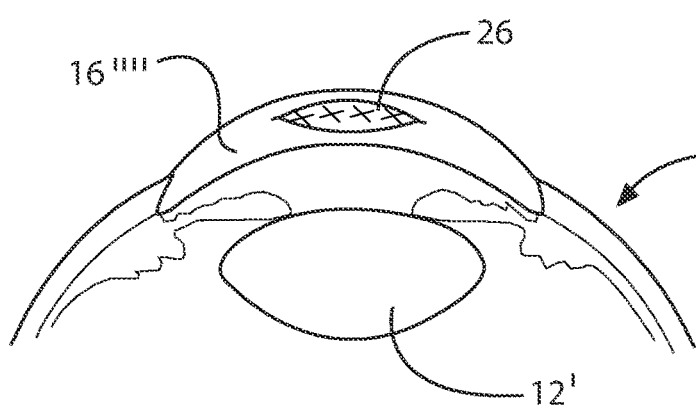
FIG. 6C is another side cross-sectional view of the host eye of FIG. 6A, which illustrates an implantation of the cross-linked lamellar lenslet into the host eye.

Finally, as shown in FIG. 6C, the cross-linked lamellar lenslet 26 is implanted into the cornea 16"" of the host eye 10"" of the patient in the location where the pocket 28 was previously formed. Because the shape of the transplant corresponds to that of the pocket 28 formed in the eye 10"", the transplant sits comfortably in its position in the host cornea 16"". As described above, after implantation of the cross-linked lamellar lenslet 26 into the eye 10"", the refractive errors of the eye 10"" have been corrected because the cross-linked lamellar lenslet 26 has been appropriately shaped to compensate for the specific refractive errors of the host eye 10"" prior to its implantation into the eye 10"". In addition, as explained above, the implantation of the cross-linked lamellar lenslet 26 provides additional stability to an eye having keratoconus, keratoglobus, a thin cornea, or abnormal corneal curvature.

Another illustrative embodiment of a corneal lenslet implantation procedure with a cross-linked cornea is shown in FIGS. 8-14. In general, the procedure illustrated in these figures involves forming a two-dimensional cut into a cornea of an eye; creating a three-dimensional pocket in the cornea of the eye, cross-linking the interior stroma, and inserting a lenslet or lens implant into the three-dimensional pocket after the internal stromal tissue has been cross-linked.

Figure 8:
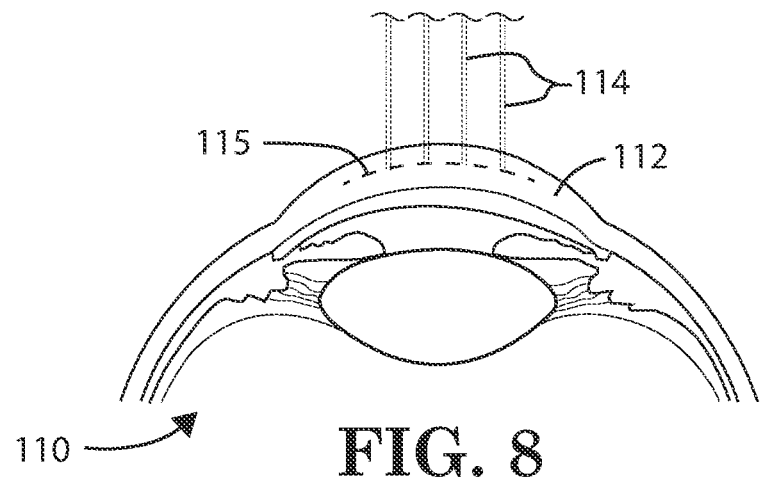
FIG. 8 is a partial side cross-sectional view illustrating the formation of a two-dimensional cut into a cornea of an eye, according to another embodiment of the invention.

Initially, in FIG. 8, the forming of a two-dimensional cut 115 into the cornea 112 of the eye 110 is diagrammatically illustrated. In particular, as shown in the illustrative embodiment of FIG. 8, the two-dimensional cut 115 is formed by making an intrastromal incision in the cornea 112 of the eye 110 using a femtosecond laser (i.e., the incision is cut in the cornea 112 using the laser beam(s) 114 emitted from the femtosecond laser). Alternatively, the two-dimensional cut 115 may be formed in the cornea 112 of the eye 110 using a knife.

Figure 9:
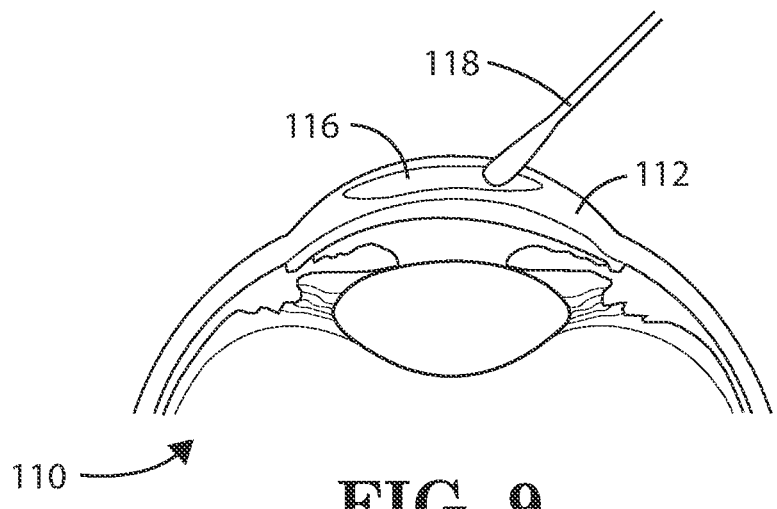
FIG. 9 is another partial side cross-sectional view of the eye of FIG. 8, which illustrates the creation of a three-dimensional pocket in the cornea of the eye.

Then, in FIG. 9, the forming of a three-dimensional corneal pocket 116 in the cornea 112 of the eye 110 is diagrammatically illustrated. In particular, as shown in the illustrative embodiment of FIG. 9, the three-dimensional corneal pocket 116 is formed by using a spatula 118. The formation of the intracorneal pocket 116 in the cornea 112 of the eye 110 allows one to gain access to the tissue surrounding the pocket 116 (i.e., the interior stromal tissue surrounding the pocket 116).

Turning again to FIGS. 8 and 9, in the illustrative embodiment, the corneal pocket 116 formed in the cornea 112 of the eye 110 may be in the form of an intrastromal corneal pocket cut into the corneal stroma. A femtosecond laser may be used to form a 2-dimensional cut into the cornea 112, which is then opened with a spatula 118 to create a 3-dimensional pocket 116. In one embodiment, a piece of the cornea 112 or a cornea which has a scar tissue is first cut with the femtosecond laser. Then, the cavity is cross-linked before filling it with an implant or inlay 128 to replace the lost tissue with a clear flexible inlay or implant 128 (see FIG. 12).

In one embodiment, a three-dimensional (3D) uniform circular, oval, or squared-shaped corneal pocket 116 is cut with a femtosecond laser and the tissue inside the pocket is removed to produce a three-dimensional (3D) pocket 116 to be cross-linked with riboflavin and implanted with a prepared implant.

Figure 10:
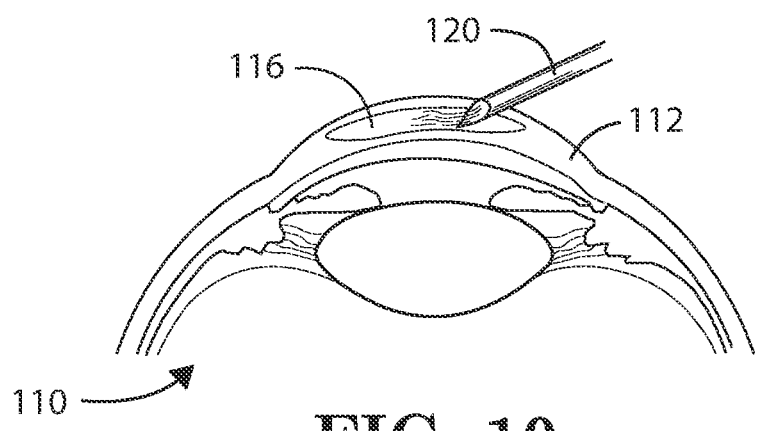
FIG. 10 is yet another partial side cross-sectional view of the eye of FIG. 8, which illustrates the injection of a photosensitizer into the three-dimensional pocket in the cornea of the eye.

After the pocket 116 is formed using the spatula 118, a photosensitizer is applied inside the three-dimensional pocket 116 so that the photosensitizer permeates the tissue surrounding the pocket 116 (see FIG. 10). The photosensitizer facilitates the cross-linking of the tissue surrounding the pocket 116. In the illustrative embodiment, the photosensitizer is injected with a needle 120 inside the stromal pocket 116 without lifting the anterior corneal stroma so as to cover the internal surface of the corneal pocket 116. In one or more embodiments, the photosensitizer or cross-linker that is injected through the needle 120 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 116 may be aspirated through the needle 120 until all, or substantially all, of the excess portion of the photosensitizer is removed from the pocket 116 (i.e., the excess cross-linker may be aspirated through the same needle so that the pocket 116 may be completely emptied or substantially emptied).

Figure 11A:
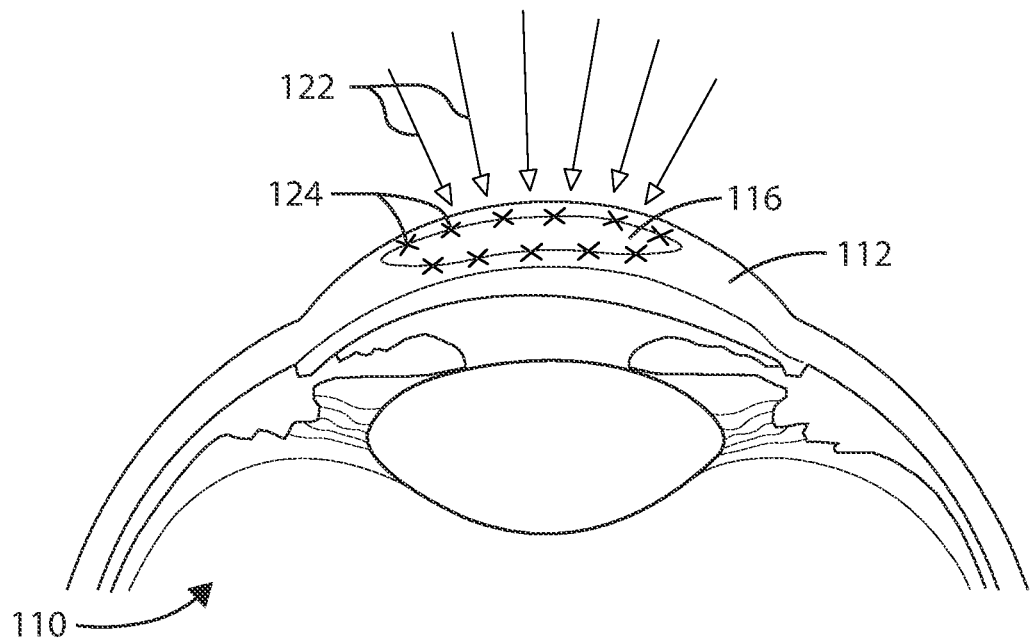
FIG. 11A is still another partial side cross-sectional view of the eye of FIG. 8, which illustrates the irradiation of the stromal tissue surrounding the three-dimensional pocket of the eye using ultraviolet radiation delivered from outside of the cornea.

Next, turning to the illustrative embodiment of FIG. 11A, shortly after the photosensitizer is applied inside the pocket 116, the cornea 112 of the eye 110 is irradiated from the outside using ultraviolet (UV) radiation 122 so as to activate cross-linkers in the portion of the tissue surrounding the three-dimensional pocket 116, and thereby stiffen the cornea 112, prevent corneal ectasia of the cornea 112, and kill cells in the portion of the tissue surrounding the pocket 116. In the illustrative embodiment, the ultraviolet light used to irradiate the cornea 112 may have a wavelength between about 370 nanometers and about 380 nanometers (or between 370 nanometers and 380 nanometers). Also, in the illustrative embodiment, only a predetermined anterior stromal portion 124 of the cornea 112 to which the photosensitizer was applied is cross-linked (i.e., the surrounding wall of the corneal pocket 116), thereby leaving an anterior portion of the cornea 112 and a posterior stromal portion of the cornea 112 uncross-linked. That is, in the illustrative embodiment, the entire corneal area inside the cornea 112 exposed to the cross-linker is selectively cross-linked, thereby leaving the anterior part of the cornea 112 and the posterior part of the stroma uncross-linked. The portion of the cornea 112 without the cross-linker is not cross-linked when exposed to the UV radiation. In an alternative embodiment, the cornea 112 may be irradiated using wavelengths of light other than UV light as an alternative to, or in addition to being irradiated using the ultraviolet (UV) radiation 122 depicted in FIG. 11A. Also, microwave radiation may be used synergistically or additively to correct non-invasively the remaining refractive error(s) of the cornea.

Figure 11B:
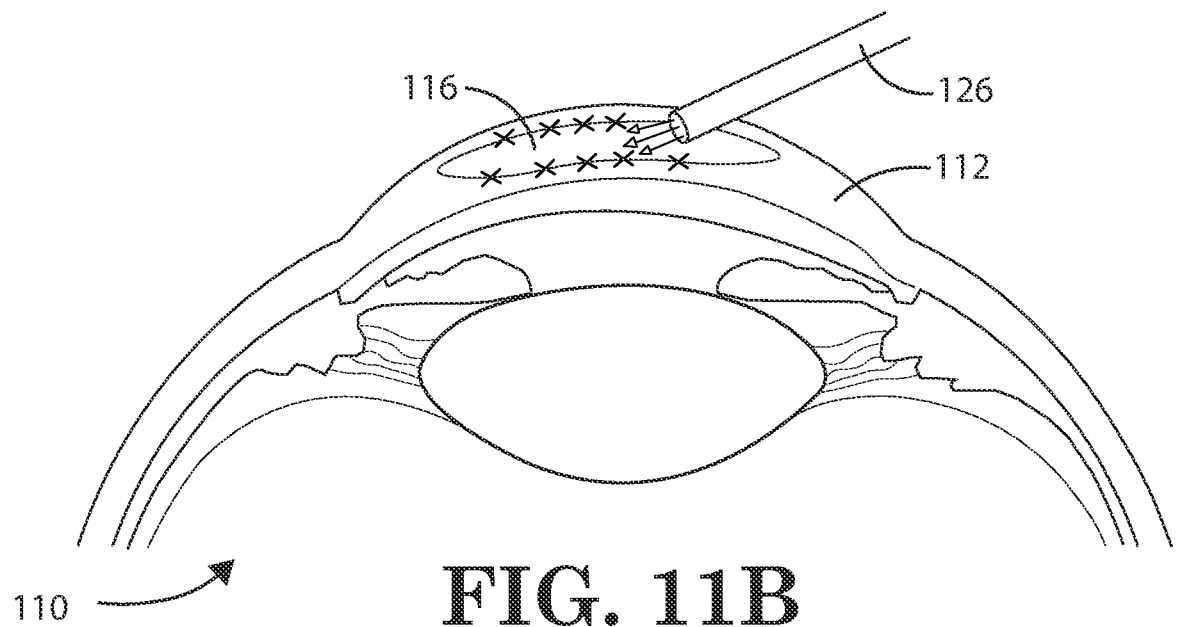
FIG. 11B is yet another partial side cross-sectional view of the eye of FIG. 8, which illustrates the irradiation of the stromal tissue surrounding the three-dimensional pocket of the eye using a fiber optic delivering ultraviolet radiation inside the three-dimensional pocket, according to an alternative embodiment of the invention.

Alternatively, as shown in FIG. 11B, a fiber optic 126 may be inserted into the corneal pocket 116 so as to apply the ultraviolet radiation and activate the photosensitizer in the wall of the corneal pocket 116. When the fiber optic 126 is used to irradiate the wall of the pocket 116, the ultraviolet radiation is applied internally, rather than externally as depicted in FIG. 11A.

Figure 12:
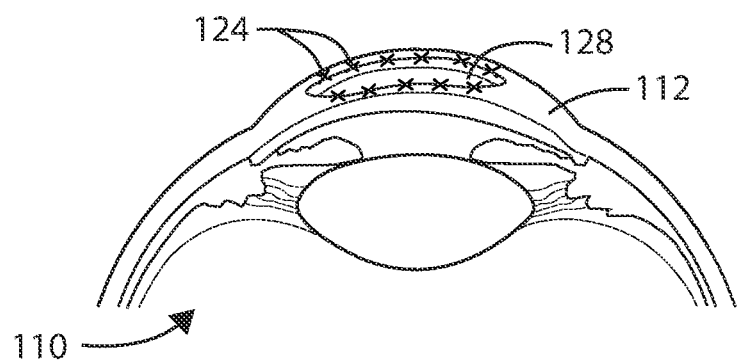
FIG. 12 is still another partial side cross-sectional view of the eye of FIG. 8, which illustrates a lens implant inserted into the pocket so as to change the refractive properties of the eye.

Now, with reference to FIG. 12, it can be seen that, after the wall of the corneal pocket 116 has been stiffened and is devoid of cellular elements by the activation of the cross-linkers, a lens implant 128 is inserted into the corneal pocket 116 in order to change the refractive properties of the eye. In particular, in the illustrated embodiment, the lens implant 128 is inserted through a small incision, and into the corneal pocket 116, using forceps or microforceps. In one or more embodiments, the lens implant 128 that is inserted inside the pocket 116 in the cornea 112 is flexible and porous. Also, in one or more embodiments, the lens implant 128 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymethacrylate, hydrogel, or a combination thereof. The surface of the lens implant 128 may have the appropriate shape to reshape the cornea 112 or the dioptric power to nullify the remaining spheric or astigmatic error of the eye. More particularly, in one or more embodiments, the lens implant 128 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In the illustrative embodiment, the irradiation of the cornea 112 using the ultraviolet (UV) radiation 122 only activates cross-linkers in the portion of the stromal tissue surrounding the three-dimensional pocket 116, and only kills the cells in the portion of the tissue surrounding the pocket 116, so as to leave only a thin layer of cross-linked collagen to prevent an immune response and rejection of the lens implant 128 and/or encapsulation by fibrocytes, while preventing post-operative dry eye formation. In addition to preventing encapsulation of the lens implant 128 by fibrocytes, the cross-linking of the stromal tissue surrounding the pocket 116 also advantageously prevents corneal haze formation around the lens implant 128. That is, the cross-linking of the stromal tissue surrounding the lens implant 128 prevents formation of myofibroblast from surrounding keratocytes, which then convert gradually to fibrocytes that appear as a haze, and then white encapsulation inside the cornea, thereby causing light scattering in front of the patient's eye.

Figure 13:
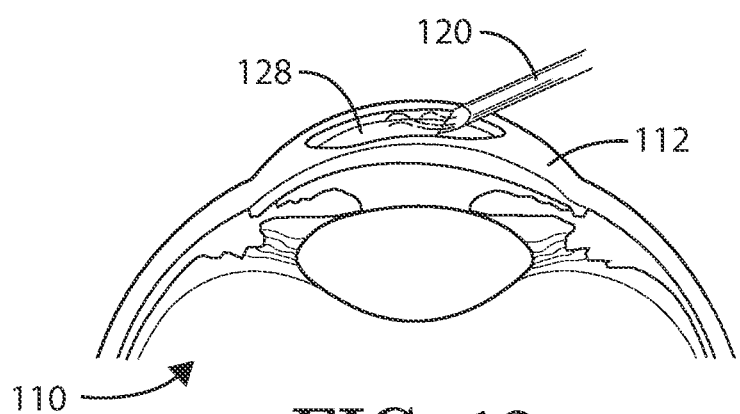
FIG. 13 is yet another partial side cross-sectional view of the eye of FIG. 8, which illustrates the reinjection of a photosensitizer into the three-dimensional pocket with the lens implant disposed therein so that the cross-linking procedure may be repeated.
Figure 14:
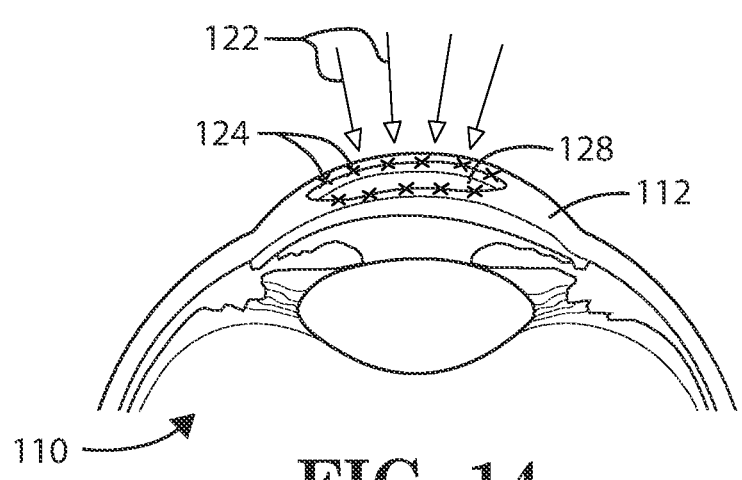
FIG. 14 is still another partial side cross-sectional view of the eye of FIG. 8, which illustrates the re-irradiation of the stromal tissue surrounding the three-dimensional pocket of the eye during the repetition of the cross-linking procedure.

As shown in FIGS. 13 and 14, the crosslinking procedure described above may be repeated after the lens implant 128 is implanted so as to prevent any cellular invasion in the area surrounding the implant 128. Initially, with reference to FIG. 13, the photosensitizer is reinjected inside the space between the lens implant 128 and the surrounding corneal tissue using a needle 120. In one or more embodiments, the needle 120 for injecting the photosensitizer may comprise a 30-32 gauge needle. Then, after the reinjection of the cross-linker, the cornea 112 is re-irradiated with ultraviolet radiation 122 to cross-link the tissue surrounding the lens implant 128 so as to prevent cellular migration towards the lens implant 128 (see FIG. 14).

In one or more embodiments, the lens implant or inlay 128 may be prepared ahead of time with known techniques, wherein the inlay 128 may be coated with a biocompatible material, such as collagen, elastin, polyethylene glycol, biotin, streptavidin, etc., or a combination thereof. The inlay 128 and the coating may be cross-linked with a photosensitizer or cross-linker, such as riboflavin, prior to being implanted into the pocket 116 in the cornea 112 of the eye.

In another embodiment, the lens implant or inlay 128 may be silicone, methacrylate, hydroxyethylmethacrylate (HEMA), or any other biocompatible transparent material, or a mixture thereof. The lens implant or inlay 128 also may be coated with materials, such as collagen or elastin, and may have a desired thickness of from 2 microns to 70 microns or more.

In yet another embodiment, the lens implant or inlay 128 is formed from an eye bank cornea, or a cross-linked eye bank cornea, etc. In general, there is a tremendous paucity of normal cadaver corneas for total or partial implants, such as for a corneal transplant of a corneal inlay. Because all the cellular elements are killed during the crosslinking of the corneal inlay, and because the corneal collagen is cross-linked and denatured, the remaining collagenous elements are not immunogenic when implanted inside the body or in the cornea of a patient. Advantageously, the prior cross-linking of the organic material, such as in the cadaver cornea, permits transplantation of the corneal inlay from an animal or human cornea or any species of animal to another animal or human for the first time without inciting a cellular or humoral response by the body, which rejects the inlay. Thus, cross-linking transparent cadaveric tissue for corneal transplantation, or as an inlay to modify of the refractive power of the eye, is highly beneficial to many patients who are on the waiting list for a corneal surgery. In addition, the surgery may be planned ahead of time without necessitating the urgency of the surgery when a fresh cadaver eye becomes available. In one or more embodiments, the collagens may be driven from the animal cornea, and cross-linked. Also, in one or more embodiments, the implant or inlay 128 may be made of cross-linked animal cornea or human cornea that is cut using a femtosecond laser to any desired shape and size, and then ablated with an excimer laser or cut with a femtosecond laser to a have a desired refractive power.

Figure 15:
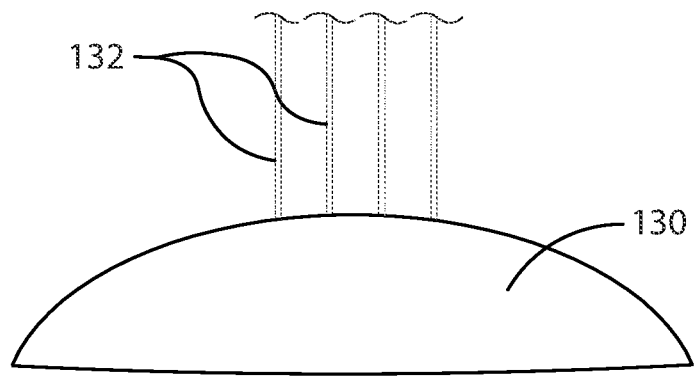
FIG. 15 is a side cross-sectional view illustrating the creation of a lens implant from an organic block of polymer using a excimer laser.
Figure 16:
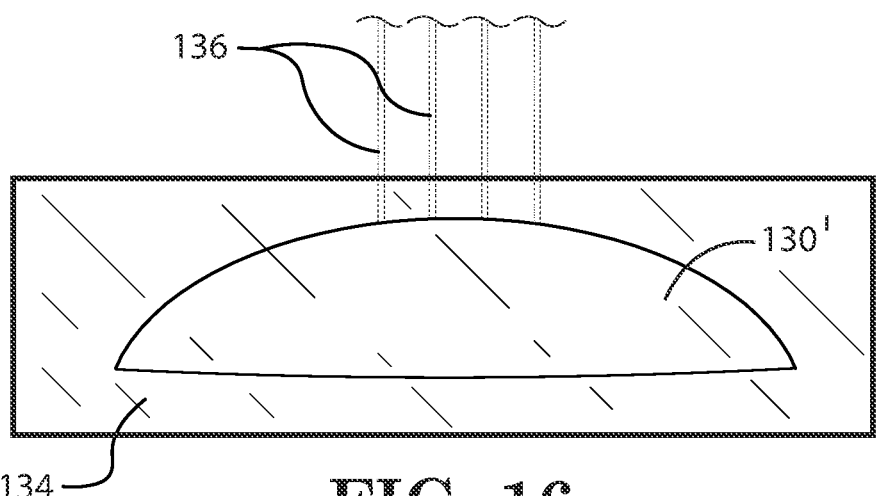
FIG. 16 is a side cross-sectional view illustrating the cutting of a lens implant from an organic block of polymer using a femtosecond laser.

For example, as shown in FIG. 15, the lens implant or inlay 130 may be formed from an organic block of a polymer (e.g., donor cornea) by cutting the lens implant 130 using an excimer laser (e.g., by using the laser beam(s) 132 emitted from the excimer laser). Alternatively, referring to FIG. 16, the lens implant or inlay 130' may be formed from an organic block 134 of a polymer (e.g., donor cornea) by cutting the lens implant 130' from the block 134 using a femtosecond laser or a computerized femto-system (e.g., by using the laser beam(s) 136 emitted from the femtosecond laser).

Figure 17:
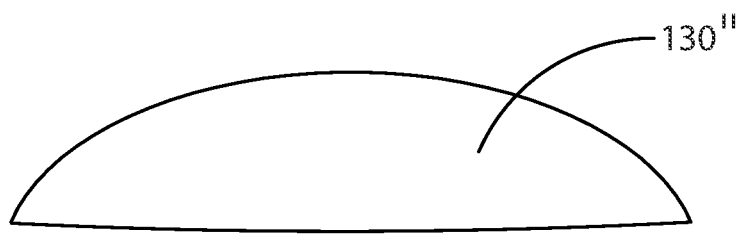
FIG. 17 is a side cross-sectional view illustrating a lens implant that has been formed using a three-dimensional printing technique or a molding technique.

In still another embodiment, as depicted in FIG. 17, the lens implant or inlay 130" is made using three-dimensional (3D) printing technology or a molding technique in order to form the lens implant or inlay 130" into the desired shape, size or thickness. The transparent material of the 3D-printed implant or inlay 130" may be coated with one or more biocompatible polymers and cross-linked prior to the implantation.

In yet another embodiment, after the implantation of an intraocular lens, the remaining refractive error of the eye may be corrected by the implantation of a lens implant or inlay 128 in the cross-linked pocket 116 of the cornea 112, thereby eliminating the need for entering the eye cavity to replace the original intraocular lens.

In still another embodiment, the remaining refractive error of the eye is corrected after an intraocular lens implantation by placing an inlay 128 on the surface of the cornea 112 of the patient while the shape of the cornea 112 is corrected with an excimer laser and wavefront optimized technology so that the patient is provided instant input on its effect on his or her vision. In this embodiment, an inlay similar to a contact lens is placed on the cornea 112 that, after correction, matches the desired refractive correction of the eye, and then, subsequently, the inlay 128 is implanted inside the cross-linked corneal pocket 116.

In yet another embodiment, the implant or inlay 128 may be ablated with an excimer laser for implantation in the cross-linked pocket 116, or after cross-linking the exposed corneal stroma in LASIK surgery.

In still another embodiment, a small amount of hyaluronic acid or a viscous fluid is injected into the pocket 116 prior to the implantation of the implant or inlay 128 so as to simplify the insertion of the implant or inlay 128 in the corneal pocket 116.

In yet another embodiment, the implant or inlay 128 is prepared having four marking holes of 0.1-2 millimeter (mm) in diameter in the inlay periphery at an equally sized distances so that the implant 128 may be rotated with a hook, if desired, after the implantation as needed to match the axis of an astigmatic error of the eye during the surgery as measured simultaneously with a wavefront technology system, such as an Optiwave Refractive Analysis (ORA) system or Holos® system, which are commercially available for measurement of astigmatism or its axis.

In still another embodiment, the implant or inlay 128 is located on the visual axis and may provide 1 to 3 times magnification for patients whose macula is affected by a disease process needing magnifying glasses for reading, such as in age-related macular degeneration, macular edema, degenerative diseases of the retina, etc. Because these eyes cannot be used normally for reading without external magnifier glasses, providing magnification by a corneal implant to one eye assists the patients in being able to read with one eye and navigate the familiar environment with their other eye.

In yet another embodiment, the surface of the cornea 112 is treated after surgery in all cases daily with an anti-inflammatory agent, such as steroids, nonsteroidal anti-inflammatory drugs (NSAIDs), immune-suppressants, such as cyclosporine A or mycophenolic acid, anti-proliferative agents, antimetabolite agents, or anti-inflammatory agents (e.g., steroids, NSAIDS, or antibiotics etc.) to prevent inflammatory processes after the corneal surgery, inlay implantation or crosslinking, while stabilizing the integrity of the implant 128 and preventing future cell growth in the organic implant or the adjacent acellular corneal tissue. In this embodiment, the medication is injected in the corneal pocket 116 along with the implantation or the implant 128 is dipped in the medication first, and then implanted in the cross-linked corneal pocket 116.

In still another embodiment, a cross-linked corneal inlay is placed over the cross-linked corneal stroma after a LASIK incision, and is abated to the desired size with an excimer laser using a topography guided ablation. By means of this procedure, the refractive power of the eye is corrected, while simultaneously providing stability to an eye prone to conceal ectasia postoperatively after a LASIK surgery. Then, the LASIK flap is placed back over the implant.

Figure 18:
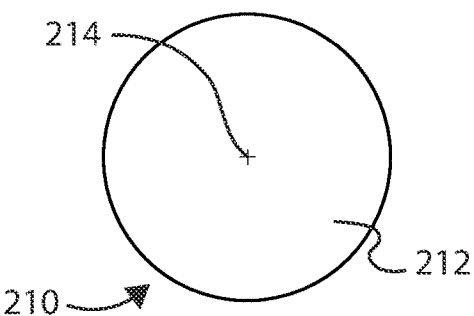
FIG. 18 is a front view of a cornea of an eye, according to yet another embodiment of the invention.

Yet another illustrative embodiment of a corneal lenslet implantation procedure with a cross-linked cornea is shown in FIGS. 18-23. In general, the procedure illustrated in these figures involves initially making an intrastromal square pocket surrounding the visual axis of the eye, and then, after forming the initial square pocket, a three-dimensional circular portion of diseased or weak stromal tissue is cut, removed, and replaced with a circular implant which fits into the circle that borders the four sides of the square. A front view of the cornea 212 of the eye 210 with the centrally-located visual axis 214 is illustrated in FIG. 18. Advantageously, in the illustrative embodiment of FIGS. 18-23, corneal tissue removal around the visual axis is greatly facilitated, and nearly perfect centration of the lens implant or inlay 220 about the visual axis is possible because the lens implant 220 fits within a depressed circular recess at the bottom of the pocket 216. As such, the undesirable decentering of the lens implant is prevented.

Figure 19:
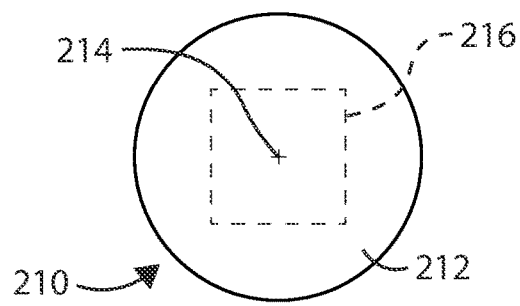
FIG. 19 is another front view of the cornea of the eye of FIG. 18, wherein a square-shaped intrastromal pocket has been formed in the cornea of the eye.

Initially, in FIG. 19, the forming of an intrastromal square-shaped pocket 216 surrounding the visual axis 214 (represented by a plus sign) in the cornea 212 of the eye 210 is diagrammatically illustrated. In particular, as shown in the illustrative embodiment of FIG. 19, the square-shaped pocket 216 is formed by making a two-dimensional intrastromal incision in the cornea 212 of the eye 210 using a femtosecond laser (i.e., the incision is cut in the cornea 212 using the laser beam(s) emitted from the femtosecond laser).

Figure 21:
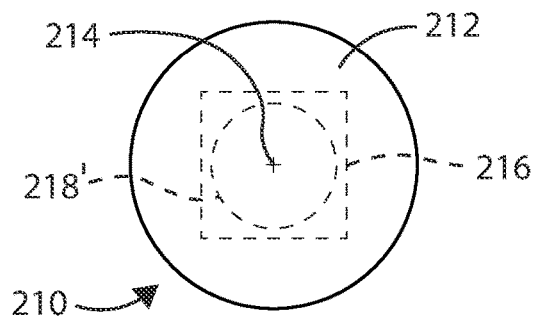
FIG. 21 is still another front view of the cornea of the eye of FIG. 18, wherein a circular three-dimensional portion of tissue having second diameter has been removed from the area within the square-shaped intrastromal pocket, the second diameter of the circular three-dimensional portion of tissue in FIG. 21 being larger than the first diameter of the circular three-dimensional portion of tissue in FIG. 20.
Figure 20:
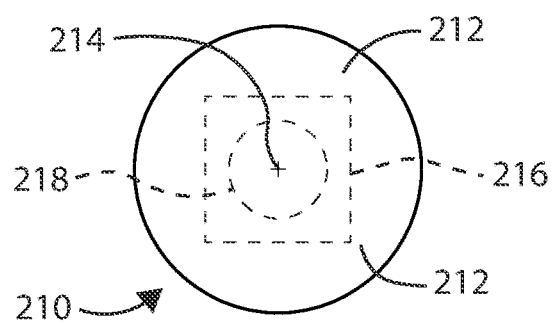
FIG. 20 is yet another front view of the cornea of the eye of FIG. 18, wherein a circular three-dimensional portion of tissue having a first diameter has been removed from the area within the square-shaped intrastromal pocket.

Then, in FIG. 20, the removal of a three-dimensional circular portion 218 of diseased or weak stromal tissue in the cornea 212 of the eye 210 is diagrammatically illustrated. In particular, as shown in the illustrative embodiment of FIG. 20, the three-dimensional circular stromal tissue portion 218 has a first diameter, which is less than a width of the square-shaped pocket 216 so that the three-dimensional circular stromal tissue portion 218 is disposed within the boundaries of the square-shaped pocket 216. The three-dimensional circular stromal tissue portion 218' depicted in FIG. 21 is generally similar to that illustrated in FIG. 20, except that the three-dimensional circular stromal tissue portion 218' depicted in FIG. 21 has a second diameter that is slightly larger than the first diameter of the three-dimensional circular stromal tissue portion 218 in FIG. 20. As such, the periphery of the three-dimensional circular stromal tissue portion 218' depicted in FIG. 21 is disposed closer to the square-shaped pocket 216, but still within the confines of the square-shaped pocket 216. In the illustrative embodiment, the three-dimensional circular stromal tissue portion 218, 218' may be removed using forceps or micro-forceps. In an exemplary embodiment, the diameter of the circular stromal tissue portion 218, 218' that is removed from the cornea 212 is between approximately 5 millimeters and approximately 8 millimeters, inclusive (or between 5 millimeters and 8 millimeters, inclusive).

In an alternative embodiment of the corneal lenslet implantation procedure, three (3) sequential cuts may be made in the stromal portion of the cornea 212 of the eye 210 using a femtosecond laser in order to form the pocket. First, a lower circular cut or incision centered about the visual axis (i.e., a lower incision with the patient in a supine position) is made using the femtosecond laser. Then, a second vertical cut is made above the lower incision using the femtosecond laser to form the side(s) of a circular cutout portion. Finally, a third square or circular cut (i.e., an upper incision) is made above the vertical cut using the femtosecond laser. In the illustrative embodiment, the lower incision is parallel to the upper incision, and the vertical cut extends between lower incision and the upper incision. In this alternative embodiment, the three-dimensional circular stromal tissue cutout portion bounded by the lower incision on the bottom thereof, the vertical cut on the side(s) thereof, and the upper incision on the top thereof is removed from the cornea 212 of the eye 210 using a pair of forceps. A cavity formed by the upper incision facilitates the removal of the three-dimensional circular stromal tissue cutout portion. As described above, the third cut or incision formed using the femtosecond laser may be an upper circular cut that is larger than the lower circular cut, rather than an upper square cut that is larger than the lower circular cut.

Figure 22:
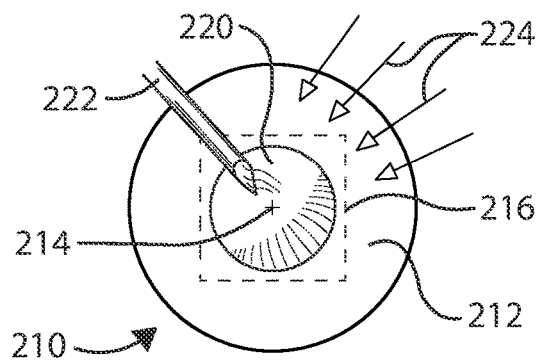
FIG. 22 is yet another front view of the cornea of the eye of FIG. 18, wherein a circular lens implant has been implanted in the area where the circular three-dimensional portion of tissue has been removed, and wherein a photosensitizer is being injected into the pocket in the cornea of the eye.

Turning to FIG. 22, after the three-dimensional circular stromal tissue portion 218, 218' is removed, a photosensitizer is applied inside the pocket 216 so that the photosensitizer permeates the tissue surrounding the pocket 216. The photosensitizer facilitates the cross-linking of the tissue surrounding the pocket 216. In the illustrative embodiment, the photosensitizer is injected with a needle 222 inside the stromal pocket 216. In one or more embodiments, the photosensitizer or cross-linker that is injected through the needle 222 inside the stromal pocket 216 comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 216 may be aspirated through the needle 222 until all, or substantially all, of the excess portion of the photosensitizer is removed from the pocket 216 (i.e., the excess cross-linker may be aspirated through the same needle 222 so that the pocket 216 may be completely emptied or substantially emptied).

Next, turning again to the illustrative embodiment of FIG. 22, shortly after the photosensitizer is applied inside the pocket 216, the cornea 212 of the eye 210 is irradiated from the outside using ultraviolet (UV) radiation 224 so as to activate cross-linkers in the portion of the tissue surrounding the three-dimensional pocket 216, and thereby stiffen the cornea 212, prevent corneal ectasia of the cornea 212, and kill cells in the portion of the tissue surrounding the pocket 216. In the illustrative embodiment, the ultraviolet light used to irradiate the cornea 212 may have a wavelength between about 370 nanometers and about 380 nanometers (or between 370 nanometers and 380 nanometers). Also, in the illustrative embodiment, only a predetermined anterior stromal portion of the cornea 212 to which the photosensitizer was applied is cross-linked (i.e., the surrounding wall of the corneal pocket 216), thereby leaving an anterior portion of the cornea 212 and a posterior stromal portion of the cornea 212 uncross-linked. That is, in the illustrative embodiment, the entire corneal area inside the cornea 212 exposed to the cross-linker is selectively cross-linked, thereby leaving the anterior part of the cornea 212 and the posterior part of the stroma uncross-linked. The portion of the cornea 212 without the cross-linker is not cross-linked when exposed to the UV radiation. In an alternative embodiment, the cornea 212 may be irradiated using wavelengths of light other than UV light as an alternative to, or in addition to being irradiated using the ultraviolet (UV) radiation 224 depicted in FIG. 22. Also, microwave radiation may be used synergistically or additively to correct non-invasively the remaining refractive error(s) of the cornea. In addition, in an alternative embodiment, the ultraviolet (UV) radiation may be applied after the implantation of the lens implant 220 to perform the crosslinking, rather than before the implantation of the lens implant 220 as described above. Further, rather than applying the ultraviolet (UV) radiation from outside the cornea 212, the stromal tissue of the pocket 216 may be irradiated from inside by means of a fiber optic, before or after the implantation of the lens implant 220.

Figure 23:
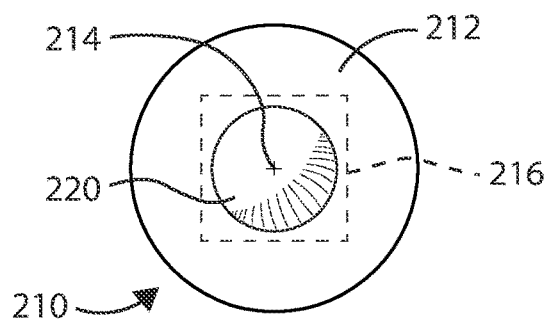
FIG. 23 is still another front view of the cornea of the eye of FIG. 18, wherein the circular lens implant is shown in the area where the circular three-dimensional portion of tissue was removed.

Now, with combined reference to FIGS. 22 and 23, it can be seen that, before or after the wall of the corneal pocket 216 has been stiffened and is devoid of cellular elements by the activation of the cross-linkers, a circular lens implant 220 is inserted into the circular recess at the bottom of the pocket 216 formed by the three-dimensional circular stromal tissue cutout portion 218, 218' that was removed. That is, the circular lens implant 220 fits within the periphery of the circular recess that borders the four sides of the squared-shaped pocket 216. In particular, in the illustrated embodiment, the circular lens implant 220 is inserted through a small incision, and into the circular recess at the bottom of the pocket 216 using forceps or microforceps. In the illustrative embodiment, the flexible lens implant 220 may be folded, inserted through the small incision, placed inside the circular recess at the bottom of the pocket 216, and finally unfolded through then small incision. In one or more embodiments, the lens implant 220 that is inserted inside the pocket 216 in the cornea 212 is flexible and porous. Also, in one or more embodiments, the lens implant 220 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymethacrylate, hydrogel, or a combination thereof.

Advantageously, the lens implant 220 of the aforedescribed illustrative embodiment always remains perfectly centered around the visual axis 214 of the eye 210, and will not move because it is disposed within the circular recess at the bottom of the pocket 216. As explained above, the lens implant 220 may be formed from an organic material, synthetic material, polymeric material, and combinations thereof. The lens implant 220 may replace either a diseased tissue or create a new refractive power for the eye 210, as explained hereinafter.

In the illustrative embodiment, the lens implant 220 may correct the refractive errors of the eye 210. The refractive error correction may be done by the lens implant 220 having a curvature that changes the corneal surface of the cornea 212. Alternatively, the lens implant 220 may have a different index of refraction that corrects the refractive power of the cornea 212. In the illustrative embodiment, the lens implant 220 may have the appropriate shape to reshape the cornea 212 or the dioptric power to nullify the remaining spheric or astigmatic error of the eye. More particularly, in one or more embodiments, the lens implant 220 may have one of: (i) a concave anterior surface to correct myopic refractive errors (i.e., a minus lens for correcting nearsightedness), (ii) a convex anterior surface to correct hyperopic refractive errors (i.e., a plus lens for correcting farsightedness), or (iii) a toric shape to correct astigmatic refractive errors.

In the illustrative embodiment, the irradiation of the cornea 212 using the ultraviolet (UV) radiation 224 only activates cross-linkers in the portion of the stromal tissue surrounding the three-dimensional pocket 216, and only kills the cells in the portion of the tissue surrounding the pocket 216, so as to leave only a thin layer of cross-linked collagen to prevent an immune response and rejection of the lens implant 220 and/or encapsulation by fibrocytes, while preventing post-operative dry eye formation. In addition to preventing encapsulation of the lens implant 220 by fibrocytes, the cross-linking of the stromal tissue surrounding the pocket 216 also advantageously prevents corneal haze formation around the lens implant 220. That is, the cross-linking of the stromal tissue surrounding the lens implant 220 prevents formation of myofibroblast from surrounding keratocytes, which then convert gradually to fibrocytes that appear as a haze, and then white encapsulation inside the cornea, thereby causing light scattering in front of the patient's eye.

It is readily apparent that the aforedescribed corneal transplant procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of above described tissue adhesives reduces the surgical procedure significantly. Moreover, the aforedescribed corneal lenslet implantation procedures modify the cornea so as to better correct ametropic conditions. Furthermore, the corneal lenslet implantation procedures described above prevent the lens implant from moving around inside the cornea once implanted, thereby ensuring that the lens implant remains centered about the visual axis of the eye.

With reference to the embodiment of FIGS. 24A-27B, a first illustrative intracorneal lens implantation procedure with a cross-linked cornea will be explained. In general, the procedure illustrated in these figures involves forming a pocket in the cornea of an eye, cross-linking the interior stroma, inserting a lens implant into the pocket, and then applying laser energy to the lens implant in the pocket using a laser to correct refractive errors of the lens implant and/or the eye in a non-invasive manner. In this embodiment, no flap is formed in the cornea 300 of the eye.

Figure 24A:
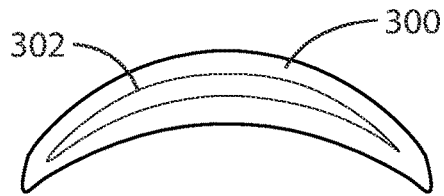
FIG. 24A is a partial side cross-sectional view illustrating the forming of a pocket in an eye, according to an embodiment of the invention.
Figure 24B:
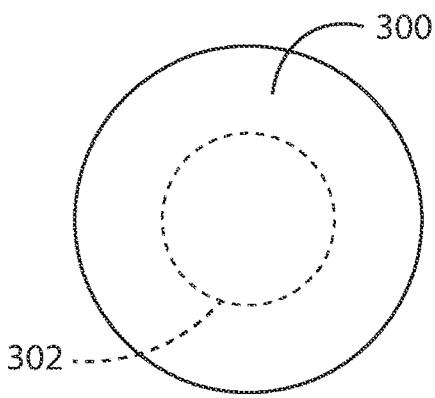
FIG. 24B is a front view of the eye of FIG. 24A, which illustrates the forming of the pocket in the eye.

In FIGS. 24A and 24B, the forming of a corneal pocket 302 in the cornea 300 of the eye is diagrammatically illustrated. FIG. 24A illustrates a cross-sectional view of the eye, whereas FIG. 24B illustrates a front view of the eye. The formation of the intracorneal pocket 302 in the cornea 300 of the eye allows one to gain access to the tissue bounding the pocket 302 (i.e., the interior stromal tissue bounding the pocket 302). In particular, as shown in the illustrative embodiment of FIG. 24A, the pocket 302 is formed by making an intrastromal incision in the cornea 300 of the eye using either a femtosecond laser (i.e., the incision is cut in the cornea 300 using the laser beam(s) emitted from the femtosecond laser) or a mechanical keratome (e.g., a mechanical microkeratome).

After the pocket 302 is cut using the femtosecond laser or mechanical keratome, a photosensitizer is applied inside the pocket so that the photosensitizer permeates the tissue bounding the pocket 302. The photosensitizer facilitates the cross-linking of the tissue bounding the pocket 302. In the illustrative embodiment, the photosensitizer is injected with a needle inside the stromal pocket without lifting the anterior corneal stroma so as to cover the internal surface of the corneal pocket 302 (e.g., as shown in FIG. 10). In one or more embodiments, the photosensitizer or cross-linker that is injected through the needle inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 302 may be aspirated through the needle until all, or substantially all, of the excess portion of the photosensitizer is removed from the pocket 302 (i.e., the excess cross-linker may be aspirated through the same needle so that the pocket 302 may be completely emptied or substantially emptied).

Figure 25A:
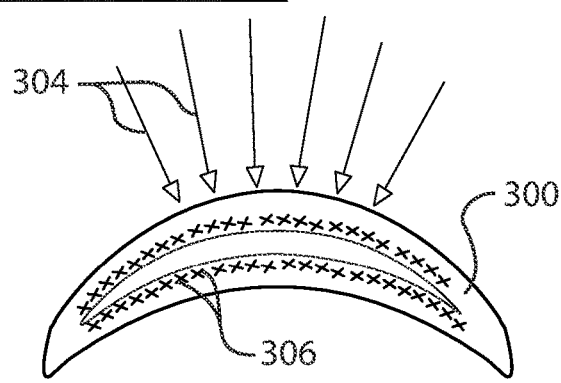
FIG. 25A is another partial side cross-sectional view of the eye of FIG. 24A, which illustrates the irradiation of the stromal tissue surrounding the pocket of the eye.

Next, turning to the illustrative embodiment of FIG. 25A, shortly after the photosensitizer is applied inside the pocket, the cornea 300 of the eye is irradiated from the outside using ultraviolet (UV) radiation 304 so as to activate cross-linkers in the portion of the tissue bounding the pocket 302, and thereby stiffen the cornea 300, prevent corneal ectasia of the cornea 300, and kill cells in the portion of the tissue bounding the pocket 302. In the illustrative embodiment, the ultraviolet light used to irradiate the cornea 300 may have a wavelength between about 370 nanometers and about 380 nanometers (or between 370 nanometers and 380 nanometers). Also, in the illustrative embodiment, only a predetermined anterior stromal portion 306 of the cornea 300 to which the photosensitizer was applied is cross-linked (i.e., the bounding wall of the corneal pocket 302), thereby leaving an anterior portion of the cornea 300 and a posterior stromal portion of the cornea 300 uncross-linked. That is, in the illustrative embodiment, the entire corneal area inside the cornea 300 exposed to the cross-linker is selectively cross-linked, thereby leaving the anterior part of the cornea 300 and the posterior part of the stroma uncross-linked. The portion of the cornea 300 without the cross-linker is not cross-linked when exposed to the UV radiation. In an alternative embodiment, the cornea 300 may be irradiated using microwaves as an alternative to, or in addition to being irradiated using the ultraviolet (UV) radiation 304 depicted in FIG. 25A.

Figure 26A:
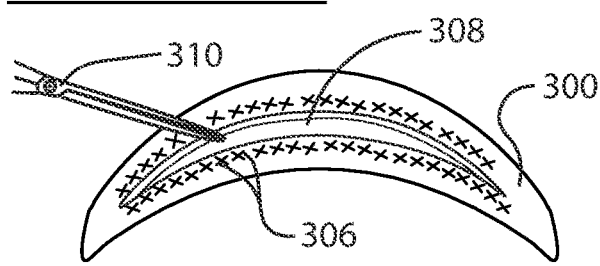
FIG. 26A is yet another partial side cross-sectional view of the eye of FIG. 24A, which illustrates the insertion of a lens implant into the pocket so as to change the refractive properties of the eye.
Figure 26B:
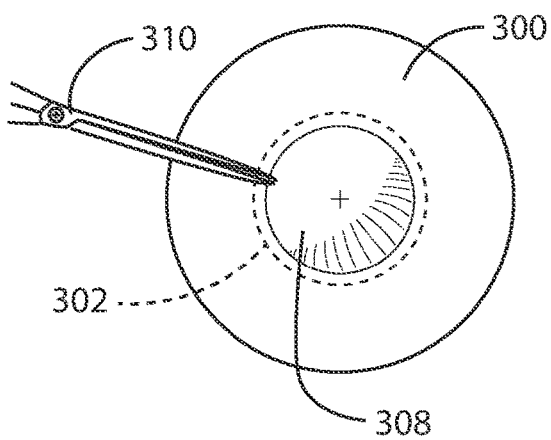
FIG. 26B is a front view of the eye of FIG. 24A, which illustrates the insertion of the lens implant into the pocket of the eye.

Now, with reference to FIGS. 26A and 26B, it can be seen that, after the cornea 300 has been stiffened and is devoid of cellular elements by the activation of the cross-linkers, a lens implant 308 is inserted into the corneal pocket 302 in order to change the refractive properties of the eye. FIG. 26A illustrates a cross-sectional view of the eye depicting the implantation of the intracorneal lens implant 308, whereas FIG. 26B illustrates a front view of the eye depicting the implantation of the intracorneal lens implant 308. In particular, in the illustrated embodiment, the lens implant 308 is inserted through a small incision, and into the corneal pocket 302, using forceps or microforceps 310. In one or more embodiments, the lens implant 308 that is inserted inside the pocket 302 in the cornea 300 is flexible and porous. Also, in one or more embodiments, the lens implant 308 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymethacrylate, hydrogel, or a combination thereof. The surface of the lens implant 308 may have the appropriate shape to reshape the cornea 300 or the dioptric power to nullify the remaining spheric or astigmatic error of the eye. More particularly, in one or more embodiments, the lens implant 308 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors. In one or more embodiment, the lens implant 308 may have any suitable shape (e.g., circular, annular, etc.) for correcting a particular error of the eye, and may be implanted in any suitable location within the cornea 300 for correcting the particular error of the eye.

In the illustrative embodiment, the irradiation of the cornea 300 using the ultraviolet (UV) radiation 304 only activates cross-linkers in the portion of the stromal tissue bounding the pocket 302, and only kills the cells in the portion of the tissue bounding the pocket 302, so as to leave only a thin layer (e.g., between 20 and 30 microns) of cross-linked collagen to prevent rejection of the lens implant 308 and/or encapsulation by fibrocytes, while preventing post-operative dry eye formation. In addition to preventing encapsulation of the lens implant 308 by fibrocytes, the cross-linking of the stromal tissue bounding the pocket 302 also advantageously prevents corneal haze formation around the lens implant 308. That is, the cross-linking of the stromal tissue surrounding the lens implant 308 prevents formation of myofibroblast from surrounding keratocytes, which then convert gradually to fibrocytes that appear as a haze, and then white encapsulation inside the cornea, thereby causing light scattering in front of the patient's eye.

In one or more further embodiments, after the lens implant 308 has been inserted into the pocket 302, an additional amount of photosensitizer (e.g., an additional amount of riboflavin) is injected into the pocket 302, and the cornea 300 is irradiated an additional time so as to further stiffen stromal tissue of the cornea and expand the area of acellular collagenous stromal tissue surrounding the lens implant 308 to prevent rejection of the lens implant 308 and/or encapsulation of the lens implant 308 by fibrocytes, while preventing post-operative dry eye formation. That is, the area of acellular collagenous stromal tissue surrounding the lens implant 308 is able to be cross-linked repeatedly through the use of additional riboflavin injections so that the area of intrastromal crosslinking may be extended, and to prevent implant rejection and cellular fibrosis formation at any time after the initial procedure. This additional cross-linking still leaves the anterior stromal nerves intact and uncross-linked so as to not produce dry eye formation.

Figure 27A:
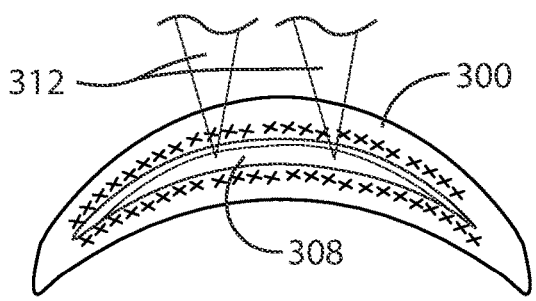
FIG. 27A is still another partial side cross-sectional view of the eye of FIG. 24A, which illustrates the application of laser energy to the lens implant in the pocket so as to correct refractive errors of the lens implant and/or the eye in a non-invasive manner.
Figure 27B:
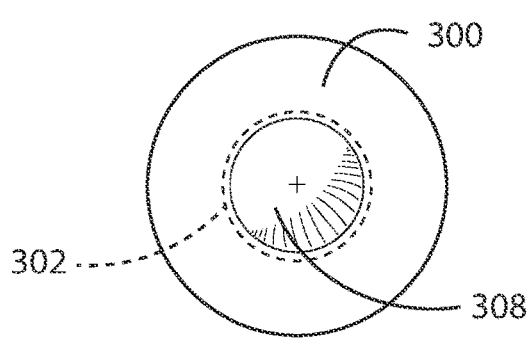
FIG. 27B is a front view of the eye of FIG. 24A, which illustrates the lens implant in the eye after the refractive power of the lens implant has been modified by the application of the laser energy.

Referring again to the illustrative embodiment of FIGS. 24A-27B, after the lens implant 308 has been inserted into the pocket 302 in the cornea 300 of the eye, laser energy is applied to the lens implant 308 in the pocket 302 using a laser 312 so as to correct refractive errors of the lens implant 308 and/or the eye in a non-invasive manner (refer to FIG. 27A). In the illustrative embodiment, a two-photon or multi-photon laser 312 is used to apply the laser energy to the lens implant 308 in the pocket 302 so as to modify the index of refraction of a discrete internal part of the lens implant 308 in a non-invasive manner, while preventing post-operative dry eye formation. In the illustrative embodiment, the laser energy applied by the two-photon or multi-photon laser has a predetermined energy level below an optical breakdown power level of the two-photon or multi-photon laser. The fast-acting, short laser pulse of the two-photon or multi-photon laser 312 is used to modify the refractive power of the lens implant 308. In the illustrative embodiment, the two-photon or multi-photon laser 312 is not used to modify the shape of the lens implant. In the illustrative embodiment, the multi-photon laser may comprise a three-photon laser, etc. Also, in the illustrative embodiment, the two-photon or multi-photon laser is a specific type of femtosecond laser.

In the illustrative embodiment, the laser beam(s) emitted by the two-photon or multi-photon laser 312 heats up the lens implant 308, and thereby modifies the index of refraction of the lens implant 308 (i.e., it creates a more positive or negative lens). Because a two-photon or multi-photon laser 312 comprises two or more laser beams that come together at the focal point of the laser, less energy is passing through the anterior corneal tissue disposed in front of the lens implant 308. Thus, advantageously, in the illustrative embodiment, the two-photon or multi-photon laser 312 does not damage the surface of the cornea or the corneal tissue anteriorly disposed relative to the lens implant 308. In the illustrative embodiment, the two-photon or multi-photon laser 312 modifies the interior of the lens implant 308 (i.e., by modifying its refractive index), but it does not modify the surface of the lens implant 308 or the corneal tissue disposed anteriorly disposed relative to the lens implant 308. In the illustrative embodiment, the laser beam(s) of the two-photon or multi-photon laser 312 may have a wavelength between about 700 nanometers and about 1100 nanometers (or between 700 nanometers and 1100 nanometers). In the illustrative embodiment, the two-photon or multi-photon laser 312 does not require a photosensitizer, and the laser beams emitted thereby may penetrate between 100 and 400 microns into the interior of the cornea.

In one or more embodiments, prior to the application of the laser energy to the lens implant 308 in the pocket 302 by the two-photon or multi-photon laser 312, a virtual model of the lens implant 308 is generated, and the two-photon or multi-photon laser 312 is focused in accordance with the virtual model. In particular, a specially programmed data processing device (i.e., a specially programmed computing device or computer) is used to generate a virtual model of the lens implant 308 so that a new index of refraction of the lens implant 308 at the focal point of the two-photon or multi-photon laser 312 is capable of being determined prior to the application of the two-photon or multi-photon laser 312. Then, the specially programmed data processing device (i.e., a specially programmed computing device or computer) is used to focus the two-photon or multi-photon laser 312 non-invasively outside the eye in accordance with the virtual model generated for the lens implant 308.

In one or more further embodiments, a femtosecond laser, a two-photon laser, or a multi-photon laser may be used to apply laser energy to the lens implant 308 in the pocket 302 in order to increase the index of refraction of a particular area of the lens implant (e.g., by creating a prismatic line on the surface of the lens or inside of the lens), and thereby convert the lens implant from a monofocal lens to a bifocal lens or trifocal lens. In these further embodiments, the particular area of the lens implant 308 that the index of refraction is increased may comprise one of: (i) an area slightly below the cornea or the central visual axis of the eye, (ii) a central area centrally located on the central visual axis of the eye, and (iii) a peripheral area circumscribing the central visual axis of the eye. For example, in one embodiment, the particular area of the lens implant 308 that is modified may be 2-3 mm in diameter to correct presbyopia in an older person. The index of refraction of the particular area of the lens implant 308 may be modified to correct myopic refractive errors (i.e., nearsightedness), hyperopic refractive errors (i.e., farsightedness), or astigmatic refractive errors. Because the lens implant 308 can be removed from the eye (e.g., using a spatula), and replaced, the entire refractive error correction process described above can be reversible, and is capable of being repeated.

Also, in one or more further embodiments, a femtosecond laser, a two-photon laser, or a multi-photon laser may be used to apply laser energy to the lens implant 308 in the pocket 302 in order to create diffractive portions within the lens implant 308, thereby resulting in a bifocal lens comprising both refractive and diffractive lens portions.

In the method described above, as illustrated in FIGS. 24A-27B, a photorefractive keratectomy (PRK) procedure is not performed on the front surface of the cornea 300 so that the front surface of the cornea 300 is not required to be ablated by an excimer laser. Also, a laser-assisted in situ keratomileusis (LASIK) procedure is not performed on the cornea 300 of FIGS. 24A-27B so that a flap is not required to be formed in the cornea 300, thereby preventing a formation of dry eye in a patient resulting from the severing of the corneal nerves supplying the front surface of the cornea 300. That is, with the method described above, it is not necessary to form a LASIK flap, which requires severing the corneal nerves about a 300 degree area of the cornea. In some patients, it can take over a year to recover from the dry eye that results from the formation of the flap during the LASIK procedure.

In a second illustrative embodiment of the intracorneal lens implantation procedure with the cross-linking of the cornea, a lens implant is soaked in a crosslinking solution prior to be inserted into the eye of the patient. As will be described in further detail hereinafter, this method generally includes soaking a lens implant in a crosslinking solution, forming a pocket in the cornea of an eye, inserting the lens implant in the pocket, cross-linking the interior stroma of the cornea, and then applying laser energy to the lens implant in the pocket using a laser to correct refractive errors of the lens implant and/or the eye in a non-invasive manner. As in the first illustrative embodiment of the intracorneal lens implantation procedure explained above, no flap is formed in the cornea of the eye. Also, the front surface of the cornea is not ablated using a PRK procedure.

Initially, in the second illustrative embodiment of the intracorneal lens implantation procedure, a lens implant is soaked in a cross-linking solution held in a container prior to its insertion into a corneal pocket in the eye so that the lens implant is pre-coated with the cross-linking solution thereon. The lens implant has a predetermined shape for changing the refractive properties of an eye, and is flexible and porous so that fluids (e.g., oxygen, electrolytes, glucose, etc.) are able to freely pass through the lens implant. In the second illustrative embodiment, the lens implant may comprise a hybrid lens implant as described above with regard to the first illustrative embodiment, or may comprise any of the other characteristics described above with regard to the lens implant 308. The coated surface of the hybrid lens implant may be organic and hydrophilic, and may formed using a desired thickness that can be cross-linked with UV light and riboflavin before or after its implantation. Also, in the second illustrative embodiment, the cross-linking solution may comprise a photosensitizer in the form of riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein).

Next, in the second illustrative embodiment of the intracorneal lens implantation procedure, a pocket is formed in the cornea of the eye. The formation of the corneal pocket in the cornea of the eye allows one to gain access to the tissue bounding the pocket (i.e., the interior stromal tissue bounding the pocket). In particular, in the second illustrative embodiment, the pocket is formed by making an intrastromal incision in the cornea of the eye either by using a femtosecond laser (i.e., the incision is cut in the cornea using the laser beam(s) emitted from the femtosecond laser) or by using a mechanical keratome (e.g., a mechanical microkeratome).

After the pocket is formed in the cornea of the eye, the lens implant with the photosensitizer provided thereon (e.g., riboflavin) is inserted inside the pocket so that the photosensitizer permeates at least a portion of the tissue bounding the pocket. In particular, in the illustrated embodiment, the lens implant is inserted into the corneal pocket through a very small incision using a pair of forceps or microforceps. The photosensitizer facilitates the cross-linking of the portion of the tissue bounding the pocket.

Then, shortly after the lens implant with the photosensitizer is inserted inside the pocket, the cornea of the eye is irradiated from the outside using ultraviolet (UV) radiation so as to activate cross-linkers in the portion of the tissue bounding the pocket, and thereby stiffen the cornea, prevent corneal ectasia of the cornea, and kill cells in the portion of the tissue bounding the pocket. In the illustrative embodiment, the ultraviolet light used to irradiate the cornea may have a wavelength between about 370 nanometers and about 380 nanometers (or between 370 nanometers and 380 nanometers). Also, in the illustrative embodiment, only a predetermined anterior stromal portion of the cornea to which the photosensitizer was applied from the lens implant is cross-linked (e.g., only the bounding wall of the corneal pocket), thereby leaving an anterior portion of the cornea and a posterior stromal portion of the cornea uncross-linked. That is, in the illustrative embodiment, the entire corneal area inside the cornea exposed to the cross-linker is selectively cross-linked, thereby leaving the anterior part of the cornea and the posterior part of the stroma uncross-linked. The portion of the cornea without the cross-linker is not cross-linked when exposed to the UV radiation. In an alternative embodiment, the cornea may be irradiated using microwaves as an alternative to, or in addition to being irradiated using ultraviolet (UV) radiation.

In the second illustrative embodiment of the intracorneal lens implantation procedure, the irradiation of the cornea using the ultraviolet (UV) radiation only activates cross-linkers in the portion of the stromal tissue bounding the pocket, and only kills the cells in the portion of the tissue bounding the pocket, so as to leave only a thin layer of cross-linked collagen to prevent rejection of the lens implant and/or encapsulation by fibrocytes, while preventing post-operative dry eye formation. In addition to preventing encapsulation of the lens implant by fibrocytes, the cross-linking of the stromal tissue bounding the pocket also advantageously prevents corneal haze formation around the lens implant. That is, the cross-linking of the stromal tissue surrounding the lens implant prevents formation of myofibroblast from surrounding keratocytes, which then convert gradually to fibrocytes that appear as a haze, and then white encapsulation inside the cornea, thereby causing light scattering in front of the patient's eye.

After the lens implant has been inserted into the pocket in the cornea of the eye, laser energy is applied to the lens implant in the pocket using a laser so as to correct refractive errors of the lens implant and/or the eye in a non-invasive manner. In the second illustrative embodiment, a two-photon or multi-photon laser is used to apply the laser energy to the lens implant in the pocket so as to modify the index of refraction of a discrete internal part of the lens implant in a non-invasive manner, while preventing post-operative dry eye formation. In the second illustrative embodiment, the laser energy applied by the two-photon or multi-photon laser has a predetermined energy level below an optical breakdown power level of the two-photon or multi-photon laser.

As described above with regard to the first illustrative embodiment of the intracorneal lens implantation procedure, prior to the application of the laser energy to the lens implant in the pocket by the two-photon or multi-photon laser, a virtual model of the lens implant may be generated, and the two-photon or multi-photon laser may be focused in accordance with the virtual model. In particular, a specially programmed data processing device (i.e., a specially programmed computing device or computer) is used to generate a virtual model of the lens implant so that a new index of refraction of the lens implant at the focal point of the two-photon or multi-photon laser is capable of being determined prior to the application of the two-photon or multi-photon laser. Then, the specially programmed data processing device (i.e., a specially programmed computing device or computer) is used to focus the two-photon or multi-photon laser non-invasively outside the eye in accordance with the virtual model generated for the lens implant.

In a third illustrative embodiment of the intracorneal lens implantation procedure with the cross-linking of the cornea, the procedure may be performed in a similar manner to that described above with regard to the second illustrative embodiment, except that the laser energy may be applied to the lens implant in the pocket by the laser prior to the irradiation of the cornea, rather than after the irradiation of the cornea as described above in the second embodiment.

In further illustrative embodiments, synthetic lenslets are created from collagen, which is modified in the process of lenslet production and subsequently after implantation, to prevent rejection of these lenslets by the host tissue. In his previous published patents (see e.g., U.S. Pat. Nos. 9,937,033, 10,278,920, 10,314,690, and 10,583,221, which are hereby incorporated by reference as if set forth in their entirety herein), the present inventor described that cross-linking the human corneal implant eliminates the human corneal immune response to the human crosslinked cornea and crosslinking the wall of the host cavity practically eliminates the host's tendency to induce an immune reaction against the implanted tissue. As described in these patents, the host's cells surrounding a corneal cavity are killed by crosslinking and the host corneal collagen in that area is also crosslinked. The crosslinking changes the molecular structure and bounding of the amino acids, peptides, and proteins creating many crosslinked bonds that make the tissue more resilient, while maintaining the transparency of the lenslet and eliminating their immunogenicity since they do not have free molecular attachments. Therefore, practically, one creates an immune privileged space inside the host cornea.

In one embodiment, the synthetic lenslet will have a compensatory refractive surface that modifies the refractive error of the host after its implantation, that is myopia, hyperopia astigmatism, and presbyopia by using either an excimer laser or a femtosecond laser with a Shack-Hartmann sensor and wavefront technology to modify the surface of the lenslet prior to its implantation in the host corneal cavity. In addition, this procedure adds to mechanical stability of the cornea because it is crosslinked.

In one embodiment, crosslinking of the synthetic inlay can be done by one or a combination of crosslinkers, such as riboflavin, xanthine, derivatives Rose Bengal, erythrosin, eosin, and phthalocyanine, porphyrin hypericin, and Rose Bengal and mixtures thereof, or other synthetic dyes, such as porphyrins, 5-aminolevulinic acid, polymeric photosensitizers, using an appropriate wavelength of a laser light.

In one embodiment, the corneal synthetic implant is produced by 3-D printing technology or molding of organic collagen material or a combination collagen with other polymers of group of chitosan, elastin, hyaluronic acid, having an index of refraction of 1.3 building a refractive lenslet of a predetermined shape that corrects the refractive power of an eye having either myopic, hyperopic, astigmatic, or presbyopia or a combination thereof, wherein the synthetic lenslet is implanted in a preformed corneal pocket created with a femtosecond laser where the synthetic lenslet along with a photosensitizer is injected inside the stromal pocket followed by crosslinking the implant and the wall of the corneal stroma by ultraviolet (UV) radiation to prevent rejection of the implant and provide resiliency to the cornea and correct refractive error of the eye.

In one embodiment, a slurry fluid containing collagen at a concentration of 1%-98% w/w or 10%-30% or 15% w/w to 50% w/w or 50% to 80% w/w or combined with other polymers, such chitosan or elastin or hyaluronic acid, etc. and a photosensitizer, such as riboflavin or Rose Bengal at concentration of 0.1%-1% injected in a corneal pocket created with a femtosecond laser wherein the synthetic collagen can correct the hyperopic refraction or presbyopia under control of a Shack-Hartmann sensor along with a photosensitizer injected inside the stromal pocket followed by crosslinking the implant and the wall of the corneal stroma by UV radiation using a UV laser at power of 3 mW/cm2 to 20 mW/cm2 for a short period or time of 1 minute to 10 minutes depending on the power of the UV laser and the concentration of the riboflavin to solidify the gel to correct hyperopia or presbyopia under the control of a Shack-Hartmann sensor and to prevent rejection of the crosslinked collagen and provide resiliency to the cornea.

In one embodiment, the corneal synthetic lenslet is produced by injection printing technology under control of a Shack-Hartmann sensor and optical coherence tomography (OCT), having a composition of organic collagen type I or a combination collagen 15% to 30% w/w or along with other polymers of group of chitosan, elastin, hyaluronic acid of less than 3% w/w and riboflavin concentration of 0.1-3% w/w or 1% w/w to 5% w/w or more is injected inside a 3-D printer unit to create a synthetic refractive lenslet which is crosslinked partially with UV radiation and injected in a corneal pocket with riboflavin and crosslinked the synthetic lenslet and the wall of the corneal stroma with the UV radiation, wherein the synthetic lenslet corrects the hyperopic, myopia, or astigmatic refraction or presbyopia and OCT.

In one embodiment, synthetic implant is made of a collagen material having a concentration of 15% w/w and other polymeric compounds are less than 1% w/w to 5% w/w or more.

In one embodiment, the synthetic lenslet contains collagen and polyethylene glycol stabilized chitosan in addition to collagen type I with some Type III collagen.

In one embodiment, the container or the mold has a predetermined surface that produces either a convex or concave or an astigmatic lenslet (see FIGS. 28-31, 34C, 34D, 35A, 35B, 36A, and 36B) in any outer shape (e.g., circular, rectangular, or square etc.). For example, a circular synthetic lenslet 412 is depicted in FIG. 30, while a circular lenslet optic 414 with a rectangular peripheral edge 416 is depicted in FIG. 31. In FIG. 28, a concave synthetic lenslet is formed from collagen 404 by using an upper mold portion 400 and a lower base mold portion 402. In FIG. 29, a convex synthetic lenslet is formed from collagen 410 by using an upper mold portion 406 and a lower base mold portion 408.

In one embodiment, the mold is from 2-14 millimeters (mm) in diameter or more.

In one embodiment, the lenslet can have a thickness of 50 microns to 2 mm or more.

Figure 32:
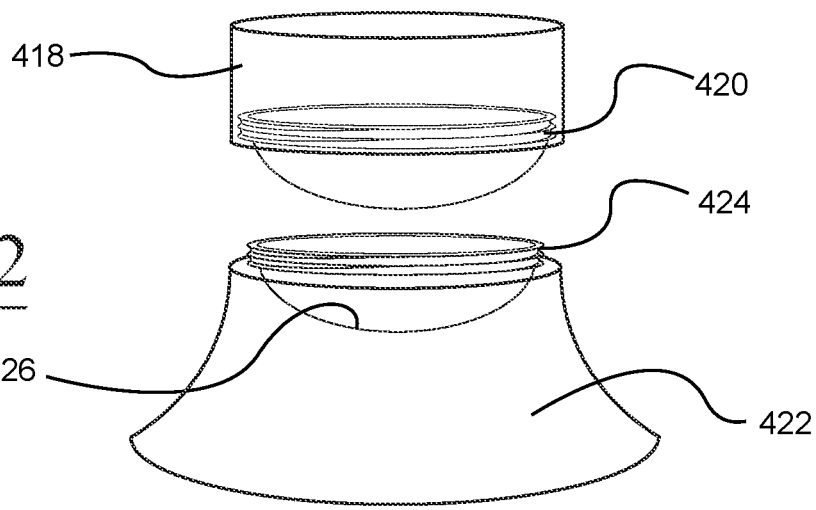
FIG. 32 is a side view of a mold with a vertical lip that is separable from the base.
Figure 33A:
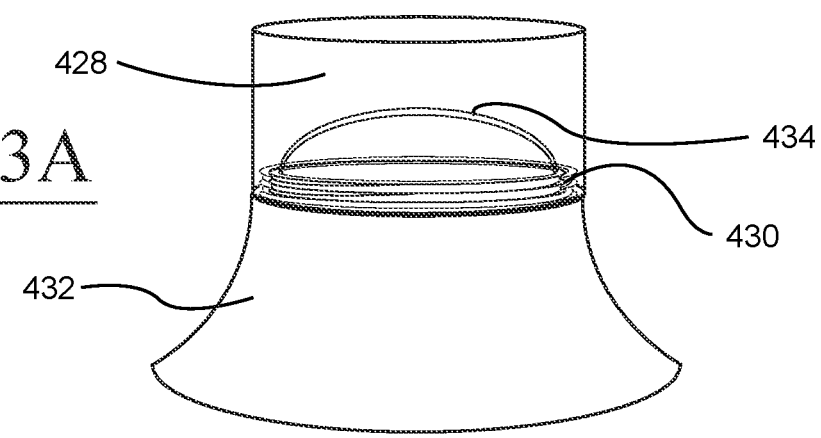
FIG. 33A is a side view of a mold with a vertical lip that is joined with the base.
Figure 34C:
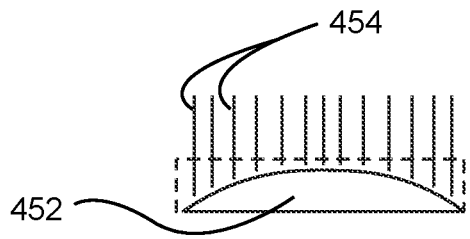
FIG. 34C is a side view of the synthetic lenslet being ablated using an excimer so as to form a convex lenslet.
Figure 34D:
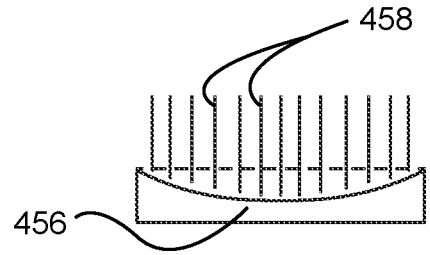
FIG. 34D is a side view of the synthetic lenslet being ablated using an excimer laser so as to form a concave lenslet.
Figure 35A:
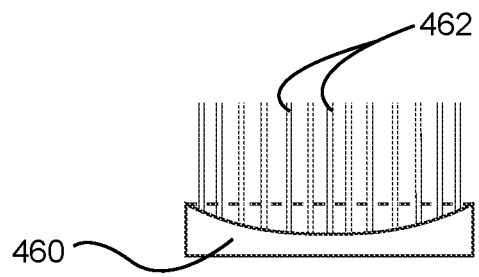
FIG. 35A is a side view of a synthetic lenslet being cut using a femtosecond laser so as to form a concave lenslet.
Figure 35B:
FIG. 35B is a side view of the synthetic concave lenslet after being cut using the femtosecond laser.
Figure 36A:
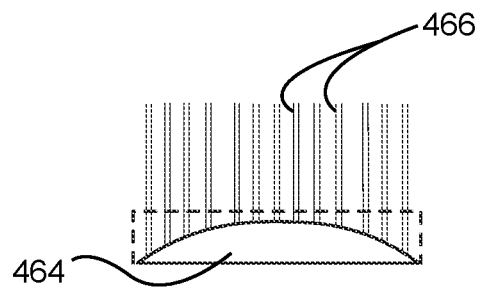
FIG. 36A is a side view of a synthetic lenslet being cut using a femtosecond laser so as to form a convex lenslet.
Figure 36B:
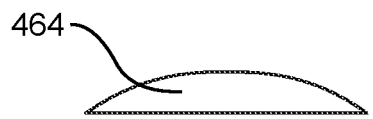
FIG. 36B is a side view of the synthetic convex lenslet after being cut using the femtosecond laser.

In one embodiment, the container has a surrounding lip which has a vertical, 90 degree or 45 degree or more tilt to the surface of the mold and extends beyond the bottom surface of the mold to create a circular stable support in which the mold is separated from the horizontally placed smooth surface such as glass (see FIGS. 32 and 33A). For example, the bases 402, 408, 422, 432, 440 of the molds depicted in FIGS. 28, 29, 32, 33A and 33B are all flared radially outward at the bottoms thereof to add more stability to the molds.

In one embodiment, the vertical lip fits in a groove at the edge of the surface of the horizontal back plate (see FIG. 32) that can be rotated in or out thereby releasing the lenslet from the lip. In FIG. 32, the base 422 of the mold has concave surface 426 for forming a concave synthetic lenslet. The upper portion 418 of the mold is threadingly engaged to the base 422 of the mold by means of the upper internal threads 420 on the upper portion 418 engaging with the corresponding external threads 424 on the base 422 of the mold. In FIG. 33A, the base 432 of the mold has convex surface 430 for forming a convex synthetic lenslet. The upper portion 428 of the mold is threadingly engaged to the base 432 of the mold by means of the upper and lower internal threads 430.

In one embodiment, the plate and the lip can be screwed in or out or in another method known in the art, releasing the formed lenslet after it is crosslinked.

In one embodiment, the corneal synthetic implant is produced by 3-D printing technology using collagen type 1 or in combination with type III collagen with or without other polymers, such as chitosan, elastin, hyaluronic acid, having an index of refraction of 1.3 and having short acting photosensitizer carbodiimide and riboflavin is used in building a lenslet of predetermined shape and/or refractive power where the carbodiimide initiate a slight crosslinking without a complete crosslinking, while the addition of riboflavin is activated after 3-D printing with UV radiation to provide a more permanent crosslinking of the lenslet that corrects the refractive power of an eye having a refractive error of myopic, hyperoptic, astigmatic, or presbyopia or a combination thereof, when implanted in a corneal pocket through a small incision made with a femtosecond laser of 1-2 mm in diameter along with 0.1% or more riboflavin solution which crosslinks the implant and the wall of the corneal stroma by UV radiation and prevents rejection of the implant and dry eye formation in the post-operative period by protecting majority of the sub-bowman nerve plexus.

In one embodiment, the two stage crosslinking permits the moderately crosslinked collaged scaffold to pass through the nozzle of the 3-D printer while the activation of the riboflavin with the UV laser subsequently completes the crosslinking of the lenslet and the wall of the corneal pocket to prevent future rejection.

In one embodiment, the lip 438 of the mold has micro holes 439 therein that permits a part of the fluid to escape if a plunger 436 (see FIG. 33B) is pressed on the synthetic collagen 442 (in the down direction of arrow 444) so that the thickness of the lenslets be reduced less than 50%-75% or less of its original volume, while the temperature of the mold is gradually increased to 37 degree C. body temperature and simultaneously the lenslet composite is irradiated with UV laser radiation of 300-420 nm wave length, preferably 375-380 nm wavelength, for a period of a few minutes which convert the liquid collagen to a collagenous resilient scaffold to make the ultimate shape of the lens stable after its implantation in a corneal pocket with further UV radiation of the lenslet and the wall of the corneal pocket to prevent its rejection by killing the corneal cells in the wall of the corneal pocket around the synthetic collagen lenslet.

In one embodiment, the shape of the collagen does not change by the crosslinking but converts a part of the collagen to crosslinked collagen scaffold and increases its biomechanical stability.

In one embodiment, the synthetic lenslet is made of mostly collagen type I alone or with some type III collagen as found in the cornea and crosslinked with a photosensitizer, such as riboflavin or Rose Bengal or other crosslinkers and UV radiation. In one embodiment, the lenslet will have a final thickness of 250 microns or less.

In one embodiment, the lenslets 452, 456 are created from +0.1 to 20.00 dioptric power, or alternatively from −0.1 to 20.00 dioptric power, or the lenslet is irradiated with an excimer laser 454, 458 (see FIGS. 34C and 34D) to create a surface from −0.1 to 20.00 dioptric power or an astigmatic refraction of −0.1 to −5.00 D or 0.1 to 5.00 D or in combination.

In one embodiment, with reference to FIGS. 34A-34D, the mold with lip 446 and base 448 is created with a parallel synthetic organic lenslet 450 while a combination of spherical or astigmatic power can be formed with an excimer laser and a Shack-Hartmann sensor to the exact dioptric power for the correction of each person's refractive error in the operating room prior to the implantation in a prepared corneal pocket that has been prepared with a femtosecond laser or mechanically.

In one embodiment, the front surface of the synthetic implant is flat and the posterior surface is convex or concave as shaped by the mold, but the lenslet is implanted with its refractive surface facing out toward the corneal epithelium and the flat surface of the lenslet lies on the posterior corneal surface of the corneal pocket.

In another embodiment, the synthetic collagen lenslet 460, 464 has a parallel surface which can be shaped to any surface curvature (e.g., concave or convex) by cutting away a part of the lens surface with a femtosecond laser 462, 466 (see FIGS. 35A, 35B, 36A, and 36B) under an OCT observation and a software to the desired lenslet's surface or refractive power to correct the refractive power of an eye, where a corneal pocket is created with a femtosecond laser in the cornea, the synthetic lenslet is soaked in a solution of riboflavin, and a small incision is made with a femtosecond laser in the corneal pocket, followed by implantation of the lenslet and injection of riboflavin in the corneal pocket and subsequent UV irradiation to completely crosslink the lenslet and its surrounding wall of the corneal stromal pocket.

In another embodiment, the solution of collagen alone or with another polymer is mixed with a photosensitizer, such as riboflavin or Rose Bengal, and is poured in a 3-D printer, and heated to 37 degrees C. and irradiated with UV radiation of 3 mW/square for 1-2 minutes to create some scaffold collagen, then the 3-D printer unit is activated with appropriate software to print out in 3-D the synthetic collagen/polymer combinations to a desired shape and refractive power with an index or the refraction of 1.3, the lenslet is implanted in the corneal stroma after soaking it in the operating room, and creating a corneal pocket injected with riboflavin and hyaluronic acid for ease of the implantation, after which the cornea is UV radiated.

In one embodiment, the synthetic lenslet is placed in an injector having a needle and the lenslet combined with hyaluronic acid as a lubricant and riboflavin simultaneously are injected inside the prepared corneal pocket followed with UV radiation to crosslink the lenslet and the wall of the corneal pocket and prevent an immune response to the lenslet.

In one embodiment, the lenslet carries slow release polymeric nanoparticles which have medication(s) such as anti-inflammatory and antibacterial medications, etc.

Since the water content of the normal cornea is about 78-80% of the cornea and the collagen component is about 15-20%, the composite of the synthetic collagen hydrogel corneal lenslet can be made in the similar range of water concentration or less, e.g., 50% to 10% or less without changing the refractive index of the cornea by crosslinking it while increasing the density of the fibrils in the lenslet.

In one embodiment, the collagen used can be Type I, Type II, Type III, Type IV, Type V, Type VI, Type XI collagen, or a combination thereof, but preferably Collagen type I.

In one embodiment, the molded lenslet is removed from the mold by removing the part around the lenslet or immersing the mold in the phosphate buffered solution containing riboflavin that penetrated the lenslet and the lenslet and the wall of the corneal cavity are crosslinked subsequently with UV radiation that crosslinks the lenslet, the wall of the corneal cavity and eliminate potential infective germs by photodynamic therapy.

In one embodiment, the composition of the collagen hydrogel, e.g., type I collagen is generated by mixing collagen powder with a desired concentrations mixture with only one crosslinker, such as riboflavin in 0.1% to 2%, etc. that does not crosslink the collagen molecules without presence of the UV light including UVA and UVB or UVC; other non-photoactivated chemical crosslinker starting crosslinking immediately after their addition to the collagen hydrogel are not as well controlled as the photoactivated ones, wherein the composite is heated to 37 degrees C. to initiate a phase transition and some febrile mesh from in the gel, then the fluid is expressed out of the mixture mechanically to the desired thickness by compressing the collagen hydrogel in the container, then exposing the hydrogel lenslet plus crosslinked or photosensitizer with UV radiation or other wavelength of light depending on the photosensitizer to achieve a lenslet texture for its refined surface modification with an excimer laser or femtosecond laser and implantation in the cornea pocket that is crosslinked with riboflavin and UV radiation.

In one embodiment, for molding, the collagen and water plus riboflavin are mixed, then compressed to reach a thickness of about ½-⅓ of its original thickness or less and crosslinked with one crosslinker, such as riboflavin/UV laser light with a power of 15-30 mW/cm2. Since the surface of the lenslet defines the refractive correction needed not its index of the refraction, the lenslet is crosslinked, then shaped by modifying its already refractive surface with an excimer laser or cut with a femtosecond laser to the desired refractive power as needed to compensate for the patient's refractive errors, using a wavefront technology and Shack-Hartmann sensor prior to its implantation.

In one embodiment, the bottom surface of the mold where the collagen gel is formed defines if the lenslet will be a convex lenslet or concave lenslet or an astigmatic lenslet, etc.

In one embodiment, the photosensitizer can be xanthine, or any other photosensitizer that generates a photodynamic effect producing singlet oxygen and reactive species that initiate crosslinking of the proteins, such as collagen when exposed to a laser light that is absorbed by the photosensitizer.

In one embodiment, the density of the lenslet collagen hydrogel mesh is increased to prevent cell migration in the lenslet by removing >95% of its water content, then further cross-linking and its surface is shaped to create a lens let that is difficult to be invaded by inflammatory cells, etc. and the corneal pocket's wall is crosslinked after lenslet implantation to create an amorphous crosslinked lenslet with a crosslinked wall of the host corneal cavity which now will not induce an immune response in the host cornea or its erosion.

In one embodiment, the lenslets are combined with polymeric slow drug release nanoparticles such as polylactic, polyglycolic acid, or a mixture thereof or polycaprolactone, polyanhydrides, micelles etc. that can penetrate the lenslet and release medication after their implantation as described in U.S. Pat. No. 10,278,920 describing a corneal drug delivery system, which is hereby incorporated by reference as if set forth in its entirety herein.

In one embodiment, the concentration of the collagen gel, e.g., 1-15% and water of 50 to 70%/riboflavin mixture or 0.1%-2% and the temperature of the medium 37 degrees C. defines how slurry the mixture of collagen gel/fibrils is to pass through the nozzle of the 3-D printer to make a 3-D lenslet to the desired width of 2-14 mm and thickness of 0.1-1 mm, and curvature of its surface, convex or concave or astigmatic, and the mechanical stability of the lenslet is defined by the degree of its crosslinking with the UV radiation of 10 mW/cm2 to 30 mW/cm2 or more after the initial lenslet is formed by the 3-D printer.

In one embodiment of the 3-D printed lenslet, the polymeric slow release nanoparticles of polylactic or polyglycolic acid, etc. are added to the collagen gel before it is pressed out of the nozzle of the 3-D printer unit, to release the medication after implantation in the corneal pocket which is crosslinked simultaneously with a photosensitizer along with implantation of the lenslet, which is crosslinked with UV radiation.

In one embodiment of the molded lenslet, the mold container is made of two sections: (a) a hollow cylindrical upper portion and (b) a base portion with a curved smooth surface that combine to make a container where the surface of the base can be convex, concave, astigmatic, or flat. In the mold, collagen type I can be used, or collagen type I in combination with collagen type II or III, and/or recombinant collagen can be used. The percentage of the collagen in a physiological solution can be from 1% to 25%, and water to which riboflavin is added at desired 0.1%-2% concentrations are pored inside the mold container, the collagen swells in the water and expands without being dissolved, thus building a collagen mesh that is not crosslinked. One can add any medications desired in a non-toxic concentration to be released as slow release polymeric nanoparticles, to the solution at this stage, so as to prevent infection or inflammation, etc.

In one embodiment, by increasing the temperature of the mold and the collagen hydrogel/riboflavin solution to 37 degrees C., small fibrils are formed inside the mold. This mixture can be used in developing a lenslet by molding or using a 3-D printer by exposing the collagen mesh to low power UV radiation such as 1-3 mW/cm2 for 1-2 minutes, the fibrils are slightly more interconnected, but they are not resilient and can be manipulated to pass through either through the nozzle of the 3-D printer or they can be used for molding.

In one embodiment of the molded lenslet, the excessive water content of the mold can be removed by using a software controlled plunger 436 that fits inside the mold and pushes the gel 442 to a desired degree forcing the fluid in the collagen hydrogel to exit through the small side holes in the wall of the mold (see FIG. 33B), thus condensing the collagen fibrils and non-crosslinked mesh to a smaller space as needed thereby reducing gradually the water content of the gel that is not completely crosslinked, but can be manipulated to become thinner to the desired thickness. The combination of increased temperature and pressure applied to the hydrogel mixture with controlled crosslinking using various amount of the UV power defines the precise degree of thickness and density or crosslinked collaged that ultimately determines its resiliency.

In one embodiment of the 3-D printed lenslet, the mixture of hydrogel at 37 degrees C. and partially crosslinked hydrogel is compressed to the degree that it can pass through the 3-D printer's nozzle to form the lenslet under the control of the printer's software and build a lenslet this is convex, concave, astigmatic, or any combination thereof and to the desired shape. At this stage, the shape or refractive power of the molded lenslet or 3-D printed lenslet can be further modified with the use of a femtosecond laser or an excimer laser under the control of software using wavefront technology and a Shack-Hartmann system to create a lenslet surface to the desired convexity, concavity, or astigmatism to correct precisely the refractive power of the patient as needed.

In one embodiment, a corneal stromal cavity in the patient's corneal stroma is prepared to the desired size so that the lenslet can be implanted in it with ease or with the help of an injector and viscoelastic material, such as heparin through a small incision made to access the cavity in the peripheral cornea.

In one embodiment, a small amount (0.05 ml) of riboflavin or other photosensitizer is injected in the stromal cavity over the lenslet to penetrate the lenslet and the wall of the cavity.

In one embodiment, ultraviolet (UV) radiation is applied at desired power of 3-30 mW/cm2 or more and a desired time of 1-5 minutes through the corneal surface to further crosslink the lenslet and the wall of the stromal cavity preventing an immune response from the host.

In a further embodiment, one uses a human cornea or cornea from genetically modified animal, such as a pig or collagen obtained mainly from a cornea (type III collagen) or a mixture of various collagen types used as inlay for creation of a supporting tissue, or modification for refractive errors or as pinhole and crosslinked because, the crosslinked corneal tissue does not inhibit transport of the water and nutrients through it regardless where in the corneal stroma it is implanted, the water and nutrients pass from the back side of cornea through the inlay (implant) to the other side of the cornea or water etc. passes from the front to the back of the cornea. As a result, the crosslinked corneal inlay does not create tissue anoxia or foreign body immune response, etc. to lead to cellular immune stimulation that would cause rejection of the inlay as seen with previous polymeric, e.g., acrylic solid lenses, when implanted inside the cornea.

Figure 37A:
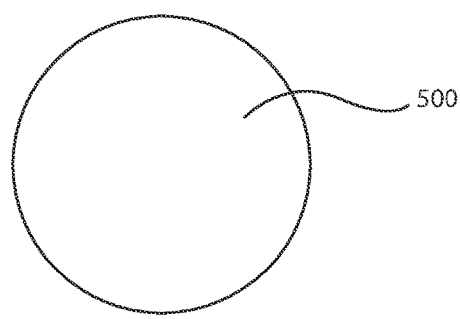
FIG. 37A is a front view of a corneal inlay, according to still another embodiment of the invention.
Figure 37B:
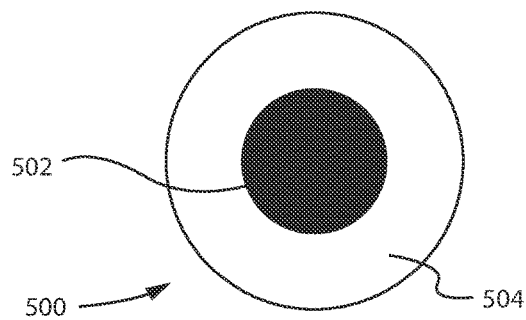
FIG. 37B is another front view of the corneal inlay after the central region has been darkened so as to be nontransparent.
Figure 37C:
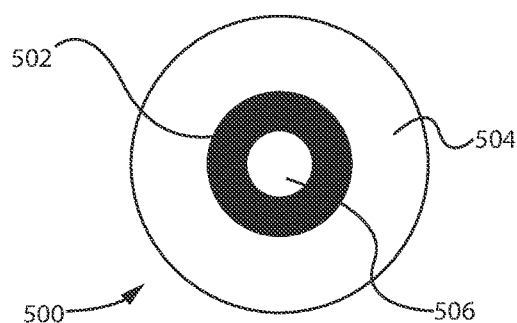
FIG. 37C is yet another front view of the corneal inlay after a pinhole has been formed in the darkened central region.
Figure 37D:
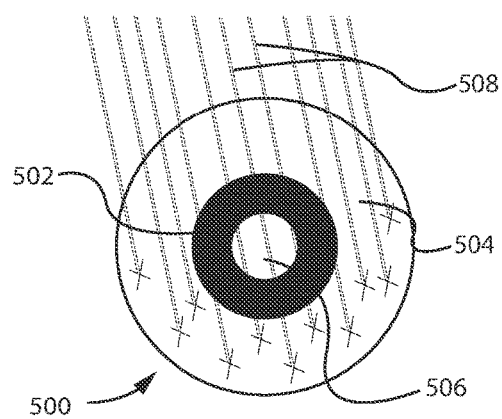
FIG. 37D is still another front view of the corneal inlay, which depicts the crosslinking of the corneal inlay using ultraviolet (UV) radiation.
Figure 37E:
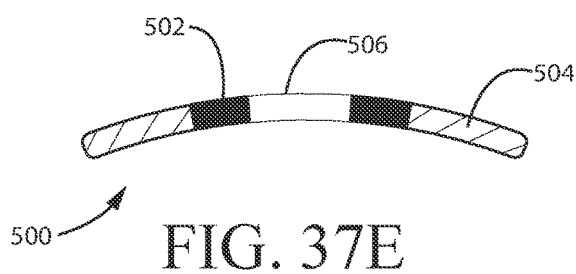
FIG. 37E is a side cross-sectional view of the corneal inlay of FIG. 37C.

In one embodiment, the corneal inlay of 5-9 mm in diameter and a thickness of 10-300 microns is obtained from human eye bank eye, or genetically modified cornea of an animal, or 3D printed corneal collagen is tattooed at its center with a biocompatible non-toxic dark or black India ink or acrylic black ink, etc., the central tattooed area 502 of the inlay 500 encompasses an area of 1 mm-5 mm (see FIGS. 37A-37C) of the inlay, and is placed in a solution of riboflavin at a concentration of 0.1-1% with or without methylene blue at concentration of 1 microgram/ml for 10 minutes or more to damage the RNA or DNA of the cells or any contaminated organism, viral, fungal, bacteria or parasites, etc. that might be present in the human or animal corneal inlay, then using a trephine or a femtosecond laser, etc., a central inlay tissue of 1-3 mm, preferably <2 mm, is cut and removed, (FIGS. 37B and 37C) leaving a rim of tattooed tissue of at least 1-1.5 mm or more having a dark tattooed area 502 around the through and through hole 506, then the inlay is crosslinked with a UV laser light 508 at a wavelength of about 320-380 nm and power of 3 mW/cm2-10 mW/cm2 for a period of 2-10 minutes or more to crosslink (see FIG. 37D) the proteins, glycoproteins, and the RNA or DNA of the cells in the inlay are crosslinked making the inlays less antigenic or not immunogenic for the host cornea, and killing all pathogenic organism that might be present in it, then the crosslinked inlay with its central hole 506 and dark rim 502 having a clear remaining peripheral area 504 (FIG. 37C) can be kept in a physiologic solution or sterile albumin etc. and or may be irradiated with gamma radiation and stored for a year or more as needed in a sterile container.

In one embodiment, a corneal inlay is made from human eye bank eye, or genetically modified cornea of pig or another animal, or 3-D printed collagen or molded from collagen and other proteins, then the central 4-5 mm area of the inlay will be tattooed with a biocompatible non-toxic dark or black India ink or acrylic black ink, etc. a hole with a diameter of <2 mm (see FIGS. 37B-37C and FIGS. 38A-38B) is cut away from its center, then the inlay is crosslinked with a photosensitizer, such as riboflavin, and irradiated with UV radiation for use as an inlay where its surface can be modified with an excimer laser after its placement over the corneal stroma under a LASIK flap to correct the refractive power of the eye for far and simultaneously create a pinhole effect in the center of the cornea to extend the focal point of the cornea for near vision in presbyopia or even in younger patients with myopia, hyperopic, with or without astigmatism or keratoconus cornea to see in focus the near objects and strengthen the mechanical stability of the cornea.

In one embodiment, as described the pinhole is created inside a corneal inlay with >5 mm in diameter then a central 4 mm tattooed area is cut with a trephine of femtosecond laser creating a hole 506 with a tattooed rim of <2 mm in diameter or more (see FIGS. 37B-37C) this organic pinhole can be implanted in the center of the cornea inside a cavity produced with a femtosecond laser using an injector to deposit the inlay in the center of the eye cavity correcting the presbyopia in older patients, the inlay and the cavity is crosslinked with riboflavin injected in the corneal cavity and irradiated with UV radiation to crosslink the inlay and the tissue around it preventing rejection of the pinhole.

Figure 42A:
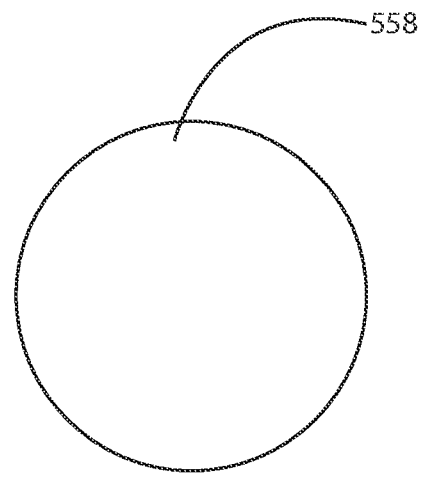
FIG. 42A is a front view of a corneal inlay, according to yet another embodiment of the invention.
Figure 42B:
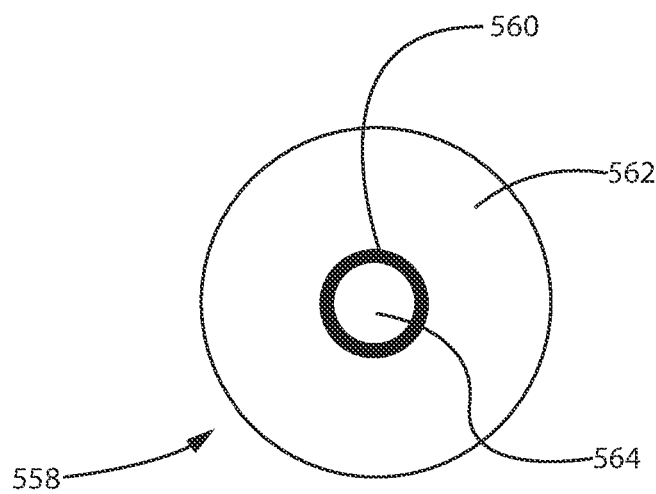
FIG. 42B is another front view of the corneal inlay after a virtual pinhole has been formed in the corneal inlay.
Figure 42C:
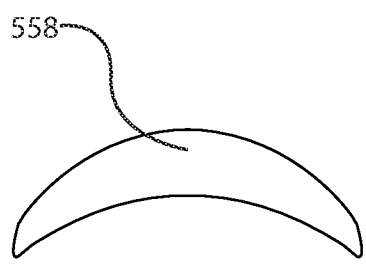
FIG. 42C is a side cross-sectional view of the corneal inlay of FIG. 42A.
Figure 42D:
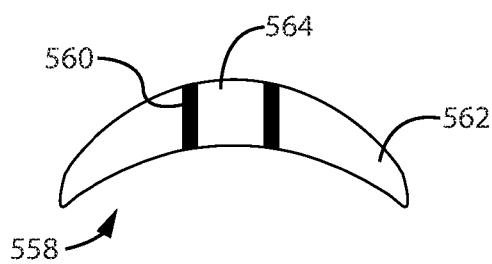
FIG. 42D is a side cross-sectional view of the corneal inlay of FIG. 42B with the virtual pinhole formed in the corneal inlay.

In one embodiment, a virtual pinhole with the diameter of 3-4 mm is created by tattooing the peripheral 2 mm diameter of the corneal inlay 558, having a thickness of 10-30 micron creating a virtual pinhole 564 (see FIGS. 42B and 42D) using a biocompatible non-toxic dark or black India ink or acrylic black ink or carbon nanoparticles etc. creating a virtual central virtual pinhole of 1-2 mm with a darkened wall and a clear peripheral area 562, then the inlay 558 is crosslinked with riboflavin with or without methylene blue combination and UV radiation, implanted in the host corneal stroma of a presbyopia eye after making a pocket in the corneal stroma with a femtosecond laser unilaterally or bilaterally that does not need to be corrected for its refractive error, where the corneal pinhole inlay provides an extended focal point for the eye permitting the person to read near and also see far objects in focus through the pinhole and the corneal pocket are simultaneously crosslinked with riboflavin and UV radiation to prevent rejection of the inlay having a virtual hole in the center of it since the center part of the inlay is not tattooed.

In one embodiment, the pinhole with the diameter of 3-5 mm with a thickness of 10-20 micron using a femtosecond, the inlay is entirely tattooed with a biocompatible non-toxic dark or black India ink or acrylic black ink etc., then the inlay is crosslinked with riboflavin and or methylene blue combination and UV radiation, using a trephine or a femtosecond laser a central hole or 1-2 mm is cut in the tattooed inlay, the pinhole dark corneal inlay is implanted inside the central part of the host cornea using an injector and hyaluronic acid after creating a 5 mm in diameter pocket in the center of the host cornea to treat presbyopia eliminating the potential rejection of the pinhole inlay.

Figure 39A:
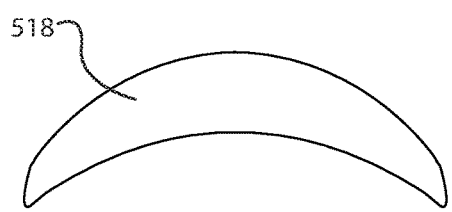
FIG. 39A is a side cross-sectional view of a cornea of an eye.
Figure 39B:
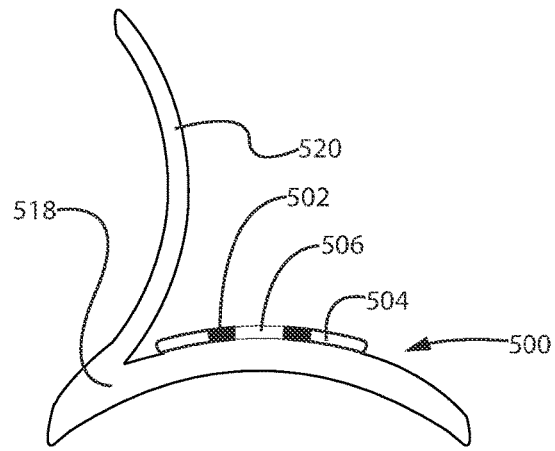
FIG. 39B is another side cross-sectional view of the cornea of FIG. 39A illustrating the formation of a corneal flap and an insertion of the corneal inlay underneath the flap.
Figure 39C:
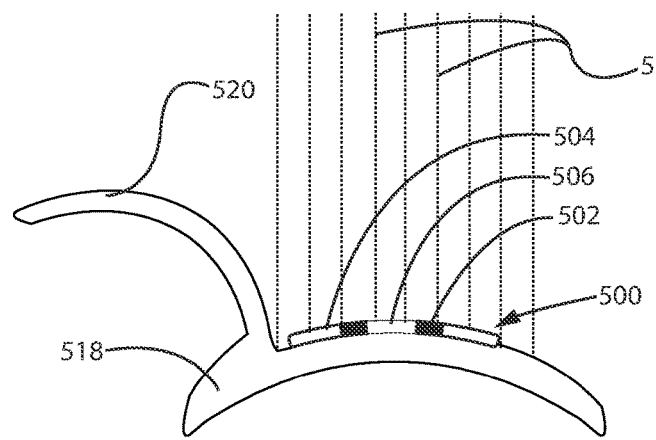
FIG. 39C is another side cross-sectional view of the cornea and corneal inlay of FIG. 39B, wherein an excimer laser is being used to ablate the corneal inlay.
Figure 39D:
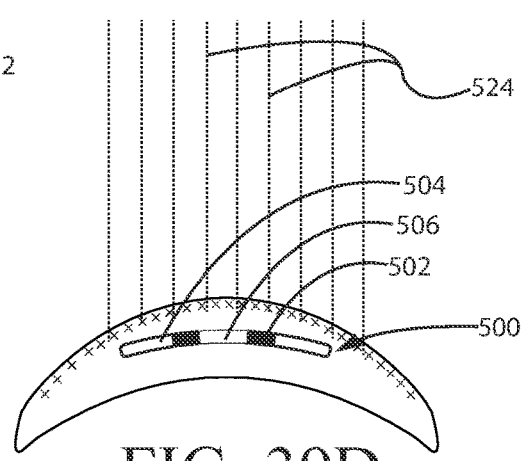
FIG. 39D is a side cross-sectional view of the cornea and corneal inlay of FIG. 39B after the flap has been closed, and the cornea and corneal inlay are being cross-linked using ultraviolet (UV) radiation.

In one embodiment, the inlay 500 from human eye bank eye, or genetically modified cornea, or 3-D printed collagen or molded from collagen and other proteins with the central virtual or a regular hole 506 and darkened tattooed rim 502 is prepared for implantation in the human cornea using a LASIK flap 520 in the host cornea 518 (see FIGS. 39A-39B). Initially, the visual axis of the eye is located on the corneal surface is marked with a pen, then using a femtosecond laser a 300 degree corneal flap 520 is prepared and turned to the side to expose the corneal stroma (see FIGS. 39A-39B), the location of the visual axis is marked with a pen on the corneal stroma and the inlay 500 is placed so that the center of the inlay's virtual/or hole coincides with the visual axis, then using an excimer laser 522 the surface of the inlay is ablated under control of wavefront technology to correct refractive error of the entire eye (see FIG. 39C), then a few drops of riboflavin is placed over the surface of the inlay 500 and the LASIK flap 520 is repositioned back over the inlay 500 to absorb the riboflavin. The cornea 518 is then irradiated with UV light 524 to crosslink the tissue surrounding the inlay and prevent its rejection (see FIG. 39D). The corneal crosslinking can be repeated with external application of riboflavin and UV light in the post-operative period to stabilize the inlay and prevent its rejection, these can be combined with topical application of any one of anti-inflammatory agents or antibiotics known to the experts.

Figure 38A:
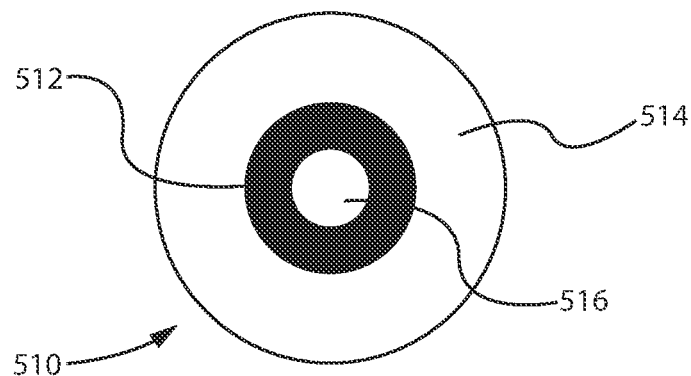
FIG. 38A is a front view of a corneal inlay, according to yet another embodiment of the invention, wherein a darkened flat ring is provided in the corneal inlay.
Figure 38B:
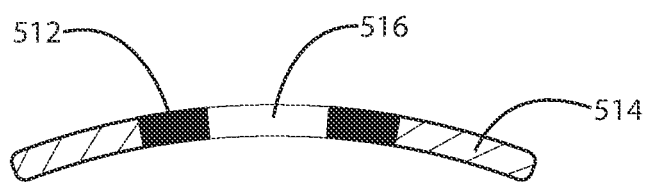
FIG. 38B is a side cross-sectional view of the corneal inlay of FIG. 38A.
Figure 38C:
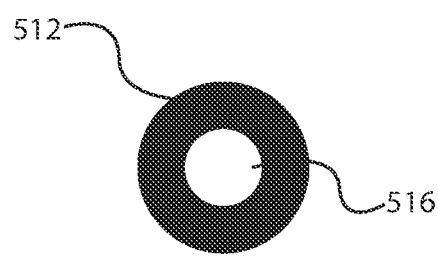
FIG. 38C is a front view of the corneal inlay of FIG. 38A with transparent peripheral portion of the corneal inlay removed.

In one embodiment, the corneal inlay with a central hole or virtual hole is 3-D printed or molded as described above to which a darkened polymeric ring 512 (see FIGS. 38A-38C) with a biocompatible non-toxic dark or black India ink or acrylic black ink etc. is produced inside the collagen molecules which will have a transparent peripheral part inlay rim 514 while an acrylic India ink etc. is injected with collagen in process of 3-D printing using the computer to form a 2-4 mm flat darkened ring 512 in the center of the inlay 510 with a transparent central part 516 including polymeric organic material with a thickness of 10-100 micron or more, while the central opening 516 or virtual aperture in the ring is between 1-2 mm and having a rim of 1-2 mm dark ring 512 surrounded by the central optically transparent collagen and outer transparent part 514 with a diameter of 5-9 mm to which riboflavin at a concentration of 0.1-1% is added after the inlay 510 is formed, in order to crosslink the inlay 510 with UV radiation prior to the implantation and kill potential pathogenic organisms and making the inlay 510 less or not immunogenic. The inlay 510 can be used under a corneal LASIK flap and its surface is modified with an excimer laser or the surface of the inlay is modified with an excimer laser prior to implantation or to be placed inside a corneal pocket, and after implantation, the inlay and its surrounding stroma is treated with riboflavin of 0.1-1% solution or more and the eye is irradiated with UV radiation for a short period of time of 1-10 minutes, and the eye is treated with topical anti-inflammatory agents.

In one embodiment, the inlay with a dark central ring is used after a LASIK flap is formed in the host cornea and the flat inlay 500 is positioned over the corneal stroma and its surface can be modified with an excimer laser 522 ablating the entire inlay to correct the refractive error (see FIGS. 39A-39D) of the eye using a wavefront technology and excimer laser 522 while providing a pinhole (ring) inside the cornea, to extend the focal point of the eye for the patient to see far and near or in between and the rest of the clear peripheral inlay 504 is treated with an excimer laser to correct refractive error of the eye such as myopia, hyperopia and astigmatism, then riboflavin solution is applied over the inlay 500 and the corneal flap 520 covers the inlay 500 while the riboflavin penetrates the inlay and the surrounding tissue of the cornea, the inlay and the surrounding tissue is simultaneously crosslinked by irradiating the eye from the outside with UV radiation 524 for 3-9 minutes and a power of laser adjusted at 3-9 miliW/cm2 to crosslink the inlay 500 and the surrounding corneal tissue preventing the rejection of the inlay. In this procedure, the refractive error of the eye is corrected on the peripheral transparent part 504 of the inlay 500 while simultaneously providing a central pinhole to extend the depth of focus for the patient looking at an object in the far or near (see FIGS. 39A-39D) with a biocompatible non-toxic dark or black India ink or acrylic black ink, etc. for correction of the refractive errors of the eye. The inlay procedure is reversible, where the inlay can be removed or replaced in the post-operative period.

In one embodiment, the inlay can be removed prior to a cataract extraction and the refractive error is corrected with an intraocular lens with or without a through central hole.

Figure 40A:
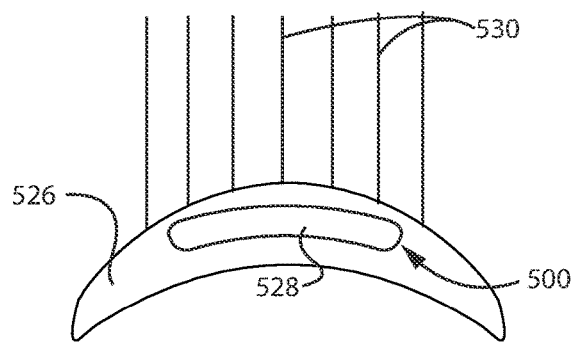
FIG. 40A is a side cross-sectional view of a cornea of an eye, which illustrates a creation of a corneal pocket therein.
Figure 40B:
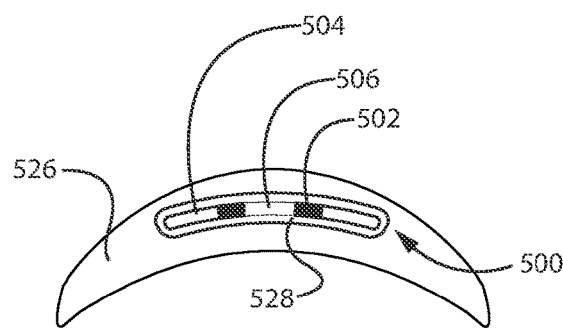
FIG. 40B is another side cross-sectional view of the cornea of FIG. 40A illustrating a corneal inlay inserted in the pocket.
Figure 40C:
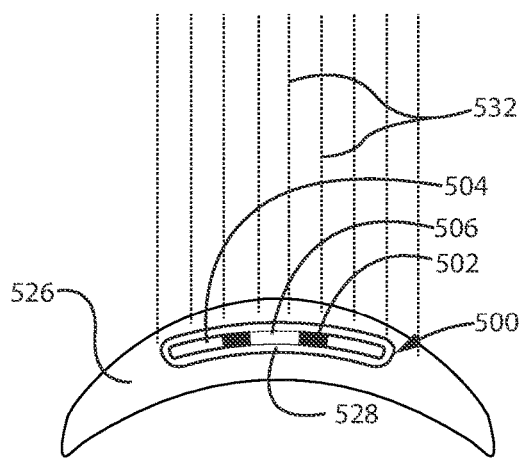
FIG. 40C is another side cross-sectional view of the cornea and corneal inlay of FIG. 40B, wherein an excimer laser is being used to ablate the corneal inlay in the pocket as part of a PRK procedure.
Figure 40D:
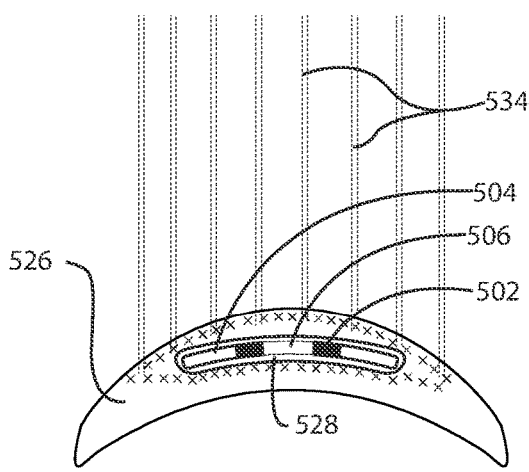
FIG. 40D is yet another side cross-sectional view of the cornea and corneal inlay of FIG. 40B, wherein the cornea and corneal inlay are being cross-linked using ultraviolet (UV) radiation.

In one embodiment, with a corneal pocket procedure where a pocket 528 is formed in the cornea 526 of the eye using a femtosecond laser 530, the crosslinked corneal inlay 500 with the central hole 506 is implanted in the pocket 528 of the cornea 526, and crosslinked as above, then after a period of time if one desires, one can perform a Photo-Refractive keratectomy (PRK) (see FIGS. 40A-40D) procedure using an excimer laser 532 with wavefront technology on the surface of the cornea 526, limited only to 5-7 mm diameter area of the corneal surface and correct the refractive error of the eye, waiting 1-2 days for the corneal epithelium to heal permitting the eye to see far and near, while preventing the side effect of the standard PRK which are severe pain or loss of corneal sensation for 1-2 months or dry eye since the corneal nerves are partially cut which significantly reduces the pain sensation in this combination procedure with LASIK, SMILE procedure, or PRK. As shown in FIG. 40D, as part of this procedure, the inlay 500 in the pocket 528 is crosslinked by irradiating the eye from the outside with UV radiation 534 for 3-9 minutes and a power of laser adjusted at 3-9 miliW/cm2 to crosslink the inlay 500 and the surrounding corneal tissue preventing the rejection of the inlay.

In one embodiment, the dark ring can be made from the eye bank cornea or genetically modified animal cornea tattooed with a biocompatible non-toxic dark or black India ink or acrylic black ink etc. or with PEGylated carbon nonospheres or nanotubes of 5-10 micron long that are mixed with polymeric nanoparticles such as PMMA, hydrogels, silicone, PVDF, polypropylene, polycarbonate, PVC, polysulfone, PEEK, polyethylene, acrylic copolymers, polystyrene, or collagen gel and crosslinked subsequently or its surface can be modified prior to implantation in the corneal stroma and combined with crosslinking the implant and the stromal tissue.

In one embodiment, for 3-D printing an organic corneal inlay and crosslinking it with riboflavin or another photosensitizer and UV radiation while the 3-D structure of the ring with carbon nanotubes or carbon nanoparticles, in acellular collagen or another polymer, absorb 99.99% of the incoming light preventing light from escaping, thus creating a very dark ring inside the inlay with a clear peripheral organic inlay.

Figure 41A:
FIG. 41A is a perspective view of a cylinder with darkened outer walls for forming a pinhole in a corneal inlay.
Figure 41B:
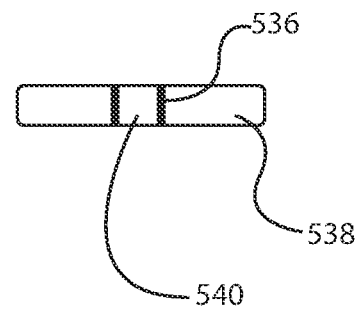
FIG. 41B is a side cross-sectional view depicting the cylinder with darkened outer walls inserted into a corneal implant.

In one embodiment, after 3-D printing or creating an inlay from human or animal cornea, a 1-2 mm wide dark cylinder 536 (see FIG. 41A) with sharp edges and a length of <400 microns, can pushed through the center of the inlay 538 to penetrate the inlay 538 (see FIG. 41B) and stay in place to act as a pinhole 540 with dark wall, and the inlay 538 is crosslinked before or after implantation to act like a pinhole 540 extending the focal point of the eye with or without correcting the refractive surface of the inlay 538.

In one embodiment, a collagenous dark ring can be made by tattooing the cornea with acrylic ink, carbon black or carbon nanoparticles or PEGylated carbon nanoparticles or PEGylated nanotubes of 5-10 micron long that are mixed with polymers such as PMMA, hydrogels, silicone, PVDF, polypropylene, polycarbonate, PVC, polysulfone, PEEK, polyethylene, acrylic copolymers, polystyrene, polyvinyl proline, polyvinyl fluorine or collagen gel and the ring placed over the host corneal stroma, having a LASIK flap before or after correcting the refractive error of the eye on the inlay's surface with an excimer laser and the inlay and the host tissue are crosslinked with the riboflavin and UV radiation to prevent rejection of the inlay.

In one embodiment, an injectable mixture of carbon nanotubes or nanoparticles made from carbon or other material and acrylic polymers etc. can be used for tattooing the corneal inlay at the inlay's central area so that a circular part of its center can be cut away with a trephine or a femtosecond laser, to create the central through and through hole in the inlay while leaving a dark rim around the hole and a clear peripheral donor cornea, that is modified with an excimer laser and crosslinked with riboflavin and UV radiation to be implanted inside a corneal pocket, which is then crosslinked with riboflavin and UV radiation.

In one embodiment, the central 1-2 mm of the transparent corneal inlay is left untouched while the tissue surrounding it is tattooed with an injectable carbon nanoparticles and an acrylic polymer to create a dark circular ring with a total width of 2-3 mm or more functioning as a virtual pinhole 560 (see FIG. 42B), without a through and through actual hole, and the surface of the remaining clear inlay of the 6-9 mm in diameter can be modified with an excimer laser to correct the refractive error of the eye before or after implantation to correct myopia, hyperopia or astigmatism while the central clear acts as a pinhole to extend the focal point of the eye for correction of presbyopia and strengthen the biomechanical property of the cornea.

In one embodiment, a circular ring of a diameter of 1-2 mm or more can be tattooed through the surface of the cornea for a distance of 10-50 microns to create a pinhole in the cornea without implanting an inlay inside the cornea, thereby creating a semi-permanent pinhole for the eye with or without standard corneal crosslinking of human animals to provide them with an extended focal point for far and near.

In one embodiment, after the inlay implantation inside the corneal stroma the inlay and its surrounding tissue is crosslinked with riboflavin and UV radiation to prevent an immune response and rejection of the inlay.

Figure 41C:
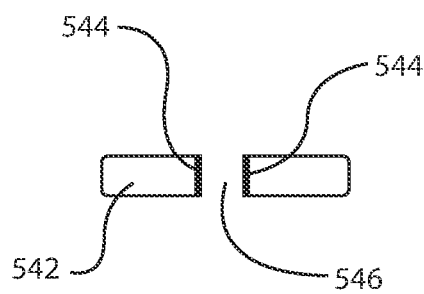
FIG. 41C is a side cross-sectional view depicting a corneal implant with a pinhole having darkened walls formed therein.
Figure 41D:
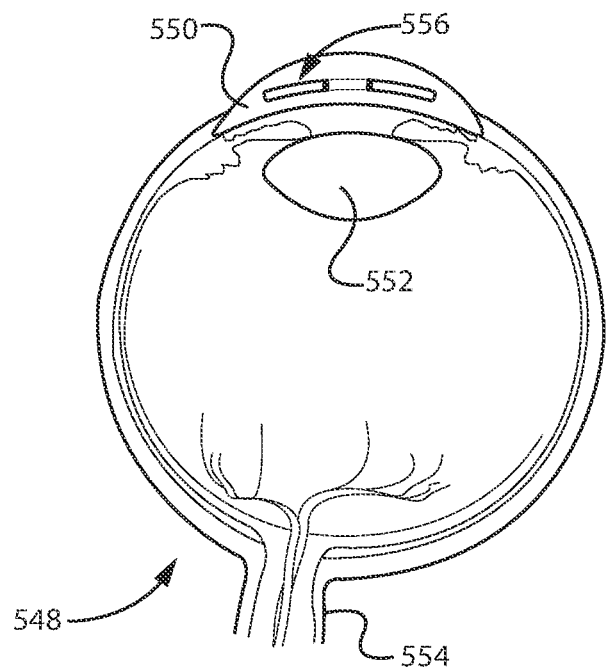
FIG. 41D is a side cross-sectional view of an eye with a corneal implant disposed in the cornea of the eye.

In one embodiment, the central pinhole 546 and its dark surrounding rim 544 of tissue occupies the central 3.5 mm in diameter part of the inlay 542 (see FIG. 41C) which has a peripheral diameter of 3.5-9 mm of clear transparent donor tissue that can be modified to correct refractive error of the eye and crosslinked. In FIG. 41D, the host eye 548 with lens 552, cornea 550, and optic nerve 554 is depicted with a corneal inlay 556 having a darkened wall or implanted darkened cylinder.

In one embodiment, the corneal inlay with a central hole and darkened peripheral hole is made by tattooing from human eye bank, or animal of genetically modified animal or not modified animal cornea or 3-D printer collagen or molded collagen with the diameter of 5 mm is cut with a trephine, or microkeratome, or femtosecond laser, the inlay is tattooed with the inlay is cut with a microkeratome or a femtosecond laser or an excimer laser to a thickness of 10 or more microns and in diameter and the inlay and the surrounding corneal tissue after implantation is crosslinked to prevent rejection.

In one embodiment, the corneal inlay is made from human eye bank eye or genetically modified animal cornea or animal corneal is made non-immunogenic with a combination of riboflavin and riboflavin solution and irradiated with a UV laser to crosslink the RNA, DNA, proteins, and glycoproteins inside the cornea to be modified subsequently with an excimer laser or femtosecond laser for implantation inside the cornea of human or an animal to correct their refractive error and crosslinked the wall of the corneal pocket to prevent their rejection by crosslinking the corneal cavity surrounding the inlay.

In another embodiment, the corneal inlay is made from the animal corneas such as dog, horse, pig or any other animals or an animal whose genes are modified first with recombinant genetic technology to prevent HLA histocompatibility response in human tissue, the inlay is initially de-cellularized with a solution of sodium dodecyl sulfate and or benzalkonium chloride, and/or treated with riboflavin and methylene blue photosensitizers and UV radiation to crosslink all cellular protein, glycoprotein and RNA and DNA of the cells and make the tissue non-antigenic while the inlay remains transparent but permits transport of water and other molecules through it, it is then processed for providing a central through hole and with or without tattooing the edges of the holes or implanting a thin polymeric darkened ring inside the inlay having the same thickness as the inlay and can be ablated with an excimer laser to modify the refractive error of the eye and after implantation and the central part of the inlay does not lift up selectively the central area of the cornea and finally the inlay and tissue surrounding the inlay are also crosslinked to kill the corneal cells and pathogens, creating an immune privileged space for the inlay implantation while correcting the refractive error for far and near and enhancing the mechanical stability of the host cornea.

In one embodiment, the animal cornea or human corneas is decellularized chemically e.g. sodium dodecyl and or undergoes a corneal crosslinking with 0.1% to 5% riboflavin and/or methylene blue at concentration of 4 mg/L or more and UV radiation at 320-380 nm wavelength and the power of 3-10 mw/cm2 to crosslink the acellular organic inlay with intercellular and cellular protein, glycoproteins and RNA or DNA, damaging all cells, bacteria, viruses, or parasites in the cornea, sterilizing the inlay maintaining the transparency of the inlay and simultaneously preventing an immune response to the inlay.

In one embodiment, the inlay is crosslinked, then is ablated with an excimer laser equipped with a wavefront technology to correct precisely the refractive power of the eye after the inlay is implanted inside the host cornea and crosslinked.

In one embodiment, the refractive power of the inlay is corrected prior to the corneal crosslinking, using an excimer laser and wavefront technology and Shack-Hartmann sensor to reshape the inlay and to correct refractive error of the patient after implantation, the inlay is crosslinked with riboflavin alone or in combination with methylene blue and irradiated with UV radiation killing the cells and potential bacteria, viruses or parasites in the corneal inlay then is implanted inside a corneal pocket created by a femtosecond laser in the host cornea, then Riboflavin is injected in the corneal pocket over the inlay and the surrounding corneal inlay is crosslinked with UV radiation from the outside the cornea to prevent an immune response from the host cornea.

In one embodiment, the procedure is as LASIK procedure, thus creating a corneal flap with a microkeratome or an excimer laser.

In another embodiment, the corneal inlay with the central hole and dark wall is implanted in a corneal pocket of human or animals such as horse dog, etc. which is created by a femtosecond laser application inside the corneal stroma at desired level inside the stroma.

In one embodiment, prior to the implantation of the corneal inlay a central hole is created in the inlay then the circular polymeric dark ring is place inside the inlay's producing through and through central hole so that the ring and the inlay have the same thickness and after their implantation the corneal flap is not elevated forward and increases the mechanical stability of the cornea in high myopia and or in keratoconus.

In one embodiment, the wall of the hole in the inlay is tattooed for a diameter of 0.5-2 mm or more as needed, the dark tattoo can be applied uniformly to either surface of the inlay with a dark none toxic particles such as carbon, the tattooing can be done before cutting out the central part of the inlay with a trephine or a femtosecond laser, leaving a the dark rim of tattooed tissue.

In the femtosecond pocket procedure, the refractive power of the eye is corrected on the inlay with the central hole prior to its implantation and the inlay and the corneal wall surrounding it is crosslinked by injection of riboflavin solution inside the corneal pocket and the eye is irradiated with UV laser light from the outside, to crosslink the inlay and the corneal tissue preventing rejection of the inlay while correcting for presbyopia and other refractive errors of the eye.

In one embodiment, in the LASIK flap procedure, the inlay with its central opening is placed over the corneal stromal after creating a corneal flap and the inlay's refractive power is corrected with an excimer laser by ablating the inlay's surface, and crosslinking it, strengthening the biomechanical stability of the cornea with the inlay in high myopia or eyes with keratoconus.

In one embodiment, in a corneal flap procedure, after correction of the refractive power of the eye on the inlay, it is crosslinked by placing a few drops of a solution of a photosensitizer, such as riboflavin, with or without methylene blue over the cornea and the corneal flap is repositioned over it, the cornea is crosslinked with UV radiation done from outside the eye, crosslinking the inlay and the surrounding stromal tissue of the flap and the corneal stroma to prevent rejection of the inlay.

In one embodiment, after making a corneal pocket with a femtosecond laser, the excimer laser ablated corneal inlay with its central ring or darkened tissue around the central opening, is implanted inside the pocket so that the central hole coincides with optical axis of the eye then a few drops of riboflavin at 0.1-1% solution alone or in combination with methylene blue at <2 mg/L concentration are injected over the inlay to penetrate it and the surrounding corneal tissue, then the eye is irradiated with UV radiation to kill all cells in the inlay or surrounding cornea along with potential bacteria, viruses or parasites while crosslinking the host corneal tissue around the corneal pocket.

In both LASIK or corneal pocket procedure, an antibiotic or an anti-inflammatory agent is applied to the cornea or injected in the corneal pocket to protect the cornea from infection, or deliver the medications by using slow release polylactic or glycolic or combination of them or other slow release compound and release them for 4-6 weeks.

In one embodiment, an inlay with a desired thickness of 20 micron to 500 micron or more and a diameter of 6-9 mm is obtained from the human eye bank or genetically modified animal or not modified, such as pig or molded or 3D printed from collagen, etc. and crosslinked to make them non-immunogenic for transplantation.

In one embodiment, the corneal inlay made of human or genetically modified animal cornea, crosslinked and its surface is modified as described, one can implant it in almost any depth from the surface of the host cornea and does not need to be implanted at a depth beyond 120-200 microns from the surface, which cannot transmit the change of the inlay surface to the corneal surface precisely which is important in refractive surgery this is followed with crosslinking the tissue around the inlay as described above.

In one embodiment, all refractive surgeries in human or animals can be done on the corneal inlay with central hole can be repeated again by replacing the old inlay with a new corneal inlay with a central hole to treat refractive errors of the eye and presbyopia simultaneously or perform a bilateral procedure permitting the patient to see stereoscopically the objects located at different focal points in front the eye and regardless of its original eye's dioptric power or age of the patient for correction of myopia, hyperopia, stigmatism, and presbyopia since no tissue is removed from the cornea, without the risk of rejection of the crosslinked inlay surrounded by crosslinked host corneal tissue and without causing corneal haze.

In one embodiment, the inlay is used to correct hyperopia by increasing the convexity of the central part of the cornea. In this embodiment, the implant is a small decellularized corneal inlay with the diameter of 2-4 mm and a thickness of 10 to 40 microns with a central hole of 1-2 mm and a tattooed 1-2 mm peripheral rim that can be implanted in a cavity of 5 mm in diameter made in the cornea with a femtosecond laser to achieve a precise dioptric power in the center of the retina which create addition convex curvature in the center with a pinhole effect with or without crosslinking the inlay and the corneal tissue achieving simultaneously a bifocal near and far vision for the patient or animal. The inlay and the surrounding tissue is crosslinked with a solution of riboflavin with or without methylene blue and UV laser radiation to prevent rejection of the inlay and simultaneous crosslinking of the adjacent corneal tissue.

In one embodiment, the genetically modified cornea can be used for full thickness corneal transplantation while crosslinking one-half or more of the thickness of the cornea with riboflavin and UV radiation.

In one embodiment, the ablatable corneal inlay for simultaneously correcting refractive errors and presbyopia is provided with a virtual hole or actual hole surrounded by a clear transparent fluid which is a permeable organic or non-organic composition, etc.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of correcting refractive errors and presbyopia in an eye of a patient using an ablatable corneal inlay, said method comprising:
    forming a darkened annular area in a central region of a corneal inlay so as to define a central pinhole for correcting presbyopia in a host eye of a patient, the darkened annular area being generally non-transparent;
    forming a flap or a pocket for receiving the corneal inlay in the cornea of the host eye of the patient;
    inserting the corneal inlay into the pocket or on stromal tissue exposed by the flap in the cornea of the host eye of the patient;
    modifying the shape of the corneal inlay using a laser so that the corneal inlay is capable of correcting refractive errors in the host eye of the patient;
    applying a photosensitizer to the cornea of the host eye of the patient so that the photosensitizer permeates at least a portion of the host corneal tissue surrounding the corneal inlay and/or at least a portion of the corneal inlay; and
    irradiating the cornea so as to activate cross-linkers in the corneal inlay and/or cross-linkers in the portion of the host corneal tissue surrounding the corneal inlay, and thereby prevent an immune response from the patient, prevent rejection of the corneal inlay by the patient, and/or strengthen the biomechanical properties of the corneal inlay;
    wherein the corneal inlay is configured to simultaneously correct refractive errors and presbyopia in the host eye of the patient.

2. The method according to claim 1, wherein the step of forming the darkened annular area in the central region of the corneal inlay comprises forming the darkened annular area in the central region of the corneal inlay by tattooing using a biocompatible, non-toxic dark or black ink.

3. The method according to claim 1, wherein the step of forming the darkened annular area in the central region of the corneal inlay comprises forming the darkened annular area in the central region of the corneal inlay by means of a darkened polymeric ring that is 3D printed with the corneal inlay.

4. The method according to claim 1, wherein the step of forming the darkened annular area in the central region of the corneal inlay comprises forming the darkened annular area in the central region of the corneal inlay by inserting a sharp-edged cylinder with darkened outer walls into the corneal inlay.

5. The method according to claim 1, wherein the step of forming the darkened annular area in the central region of the corneal inlay comprises forming the darkened annular area in the central region of the corneal inlay by creating a central aperture in the corneal inlay, and then subsequently tattooing a bounding wall of the central aperture using a biocompatible, non-toxic dark or black ink.

6. The method according to claim 1, wherein the step of forming the darkened annular area in the central region of the corneal inlay comprises forming the darkened annular area in the central region of the corneal inlay by creating a virtual pinhole in the corneal inlay by tattooing using a biocompatible, non-toxic dark or black ink or by 3D printing the virtual pinhole.

7. The method according to claim 1, wherein the corneal inlay is formed from a collagen solution using a mold or a 3-D printer, the mold or the 3-D printer being configured to form the corneal inlay into a predetermined shape for correcting a particular refractive error of the patient.

8. The method according to claim 7, wherein the corneal inlay is formed using the 3-D printer, the 3-D printer including a nozzle for forming the corneal inlay in layers from a collagen solution, and the 3-D printer being under the control of a data processing device so as to form the corneal inlay into a predetermined shape for correcting a particular refractive error of the patient.

9. The method according to claim 1, wherein the step of applying the photosensitizer to the cornea of the host eye of the patient further comprises applying riboflavin to the cornea of the host eye of the patient so that the riboflavin permeates at least the portion of the host corneal tissue surrounding the corneal inlay and/or at least the portion of the corneal inlay; and wherein the step of irradiating the cornea so as to activate cross-linkers in the corneal inlay and/or cross-linkers in the portion of the host corneal tissue surrounding the corneal inlay further comprises irradiating the cornea with ultraviolet radiation so as to activate cross-linkers in the corneal inlay and/or cross-linkers in the portion of the host corneal tissue surrounding the corneal inlay.

10. The method according to claim 1, wherein the step of modifying the shape of the corneal inlay using the laser comprises ablating the corneal inlay using an excimer laser or a femtosecond laser under the control of a Shack-Hartmann wavefront system and a data processing device so as to modify the corneal inlay to the desired refractive power so that the corneal inlay corrects refractive error of the eye as desired for hyperopia, myopia, astigmatism, or presbyopia after its implantation.

11. The method according to claim 1, wherein the corneal inlay is formed from an animal cornea.

12. The method according to claim 11, wherein the corneal inlay is decellularized using chemical means, the chemical means for destroying the cellular elements in the corneal inlay are selected from the group consisting of ethanol, glycerol, acids, alkalis, peracetic acid, ammonium hydroxide ionic detergents, sodium dodecyl sulfate, sodium deoxycholate non-ionic detergents, zwitterionic detergents, Triton X-100, benzalkonium chloride, Igepal, genipin, and combinations thereof.

13. The method according to claim 1, wherein the corneal inlay is formed from a human cornea.

14. The method according to claim 1, wherein the step of forming a flap or a pocket for receiving the corneal inlay in the cornea of the host eye of the patient comprises forming the flap in the cornea of the host eye of the patient for receiving the corneal inlay.

15. The method according to claim 1, wherein the step of forming a flap or a pocket for receiving the corneal inlay in the cornea of the host eye of the patient comprises forming the pocket in the cornea of the host eye of the patient for receiving the corneal inlay.

* * * * *